US012564228B2

(12) United States Patent
Jayaraman et al.

(10) Patent No.: US 12,564,228 B2
(45) Date of Patent: Mar. 3, 2026

(54) RESPIRATORY PROTECTIVE DEVICE WITH CONTINUOUS FIT MONITORING

(71) Applicant: Georgia Tech Research Corporation, Atlanta, GA (US)

(72) Inventors: Sundaresan Jayaraman, Atlanta, GA (US); Sungmee Park, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 417 days.

(21) Appl. No.: 18/162,312

(22) Filed: Jan. 31, 2023

(65) Prior Publication Data

US 2023/0285784 A1 Sep. 14, 2023

Related U.S. Application Data

(60) Provisional application No. 63/304,893, filed on Jan. 31, 2022.

(51) Int. Cl.
| | |
|---|---|
| *A41D 13/11* | (2006.01) |
| *A62B 18/02* | (2006.01) |
| *A62B 18/08* | (2006.01) |
| *A62B 27/00* | (2006.01) |

(52) U.S. Cl.
CPC ...... *A41D 13/1161* (2013.01); *A41D 13/1107* (2013.01); *A41D 13/1153* (2013.01); *A62B 18/02* (2013.01); *A62B 18/08* (2013.01); *A62B 27/00* (2013.01); *A61M 2207/10* (2013.01)

(58) Field of Classification Search
CPC ............ A41D 13/1161; A41D 13/1107; A41D 13/1153; A62B 18/02; A62B 18/08; A62B 27/00; A61M 2207/10
See application file for complete search history.

(56) References Cited

U.S. PATENT DOCUMENTS

| | | | | |
|---|---|---|---|---|
| 8,573,199 | B2 * | 11/2013 | King ...................... | A62B 27/00 |
| | | | | 128/206.28 |
| 10,646,731 | B2 | 5/2020 | Jayaraman et al. | |
| 10,646,732 | B2 * | 5/2020 | Rachapudi ............. | A62B 9/006 |
| 10,843,015 | B2 * | 11/2020 | Patil ...................... | A62B 9/006 |
| 2017/0361045 | A1 * | 12/2017 | Fu ..................... | A61M 16/0066 |

(Continued)

OTHER PUBLICATIONS

Institute of Medicine. 2008. Preparing for an Influenza Pandemic: Personal Protective Equipment for Healthcare Workers. Washington, DC, https://doi.org/10.17226/11980.

(Continued)

*Primary Examiner* — David Z Huang
(74) *Attorney, Agent, or Firm* — Meunier Carlin & Curfman LLC

(57) ABSTRACT

An exemplary system and method are disclosed for a respiratory protective device configured to continuously monitor, via an integrated sensor network embedded in the device's frame, the fit or proper particulate-filtering operation of the respiratory protective device. The system can ensure proper operation of respiratory protective device while providing monitoring and tracking of the fit to ensure personal safety for users wearing the device. In some embodiments, the system can monitor, track, and aggregate the data to present via a user interface to the user.

21 Claims, 26 Drawing Sheets

(56)                    References Cited

U.S. PATENT DOCUMENTS

2021/0361003 A1* 11/2021 Barr ................... B01D 39/2017
2021/0402222 A1* 12/2021 Kwon ................. A62B 18/025

OTHER PUBLICATIONS

Institute of Medicine. 2006. Reusability of Facemasks During an Influenza Pandemic: Facing the Flu. Washington, DC, https://doi.org/10.17226/11637. Read free on-line: https://nap.nationalacademies.org/read/11637/chapter/1.

National Academies of Sciences, Engineering, and Medicine. 2019. Reusable Elastomeric Respirators in Health Care: Considerations for Routine and Surge Use. Washington, DC: The National Academies Press. https://doi.org/10.17226/25275. Read free on-line: https://nap.nationalacademies.org/read/25275/chapter/1.

Roberge, R., Niezgoda, G., Benson, S., Analysis of Forces Generated by N95 Filtering Facepiece Respirator Tethering Devices: A Pilot Study, Journal of Occupational and Environmental Hygiene, 9 (8), 2012, pp. 527-533.

Zhuang, Z., Bergman, M., Lei, Z., Niezgoda, G. & Shaffer, R. (2017) Recommended test methods and pass/fail criteria for a respirator fit capability test of half-mask air-purifying respirators. J. Occup. Environ. Hyg. 14, 473-481. https://doi.org/10.1080/15459624.2017.1296233.

Yang J, Dai J, Zhuang Z. Simulating the interaction between a respirator and a headform using LS-DYNA. Computer-Aided Design Appl. 2009; 6(4):539-551.

Protecting facial skin under N95 face masks, National Pressure Injury Advisory Panel, https://cdn.ymaws.com/npiap.com/resource/resmgr/position_statements/NPIAP_-_Mask_Injury_Infograp.pdf, Last Accessed: Jun. 19, 2020.

Stokowski, L.A. (2020) A Step-by-Step Guide to Preventing PPE-Related Skin Damage. MedScape. Retrieved from https://www.medscape.com/viewarticle/929590.

Lam, U-Nee., Siddik, Nur., Yussof, Shah., and Ibrahim, S. (2020) N95 respirator associated pressure ulcer amongst COVID-19 health care workers, Int Wound J. October; 17(5): 1525-1527, doi: 10.1111/iwj.13398.

Oot-Giromini B, Bidwell FC, Heller NB, et al. Pressure ulcer prevention versus treatment, comparative product cost study. Decubitus 1989; 2(3):52-4.

Cleaning and Disinfecting 3M Reusable Elastomeric Half and Full Facepiece Respirators following Potential Exposure to Coronaviruses, https://multimedia.3m.com/mws/media/1793959O/cleaning-and-disinfecting-3m-reusable-respirators-following-potential-exposure-to-coronaviruses.pdf.

Cai, M., Li., H., Shen, S., Wang, Y, and Yang, Q. (2018) "Customized design and 3D printing of face seal for an N95 filtering facepiece respirator", Journal of Occupational and Environmental Hygiene, 15:3, 226-234, https://doi.org/10.1080/15459624.2017.1411598.

Zhuang, Z., & Bradtmiller, B. (2005) A Head-and-Face Anthropometric Survey of U.S. Respirator Users. J Occup Environ Hyg. Nov; 2 (11):567-76. DOI: https://10.1080/15459620500324727. PMID: 16223715.

3dMD. (2020) Retrieved from https://3dmd.com/products/.

Granta. (2020) Chart from CES EduPack, ANSYS Granta. 2019.

Ashby. (2008) The CES EduPack Database of Natural and Man-Made Materials, Version 1.0, Granta Design, Cambridge, UK, Jan. 2008.

Shore. (2020) "Shore hardness scale," https://www.smooth-on.com/page/durometer-shore-hardness-scale/, Last Accessed: Nov. 14, 2020.

Formlabs. (2022a) Elastic 50A, https://formlabs.com/materials/flexible-elastic/. Last Accessed: Jun. 19, 2022.

Carbon 3D. (2022) SIL 30, https://www.carbon3d.com/materials/sil-30, Last Accessed: Jun. 18, 2022.

Dow. (2022) Silastic™ 3D 3335 Liquid Silicone Rubber, https://www.dow.com/en-us/pdp.silastic-3-d-3335-liquid-silicone-rubber-lsr.4137603z.html?productCatalogFlag=1#overview, Last Accessed: Jun. 18, 2022.

Elkem. (2019) Silicones 3D Flyer Industrial, https://www.elkem.com/silicones/brands/amsil/, Last Accessed: Jun. 18, 2022.

* cited by examiner

Ø = 6.00 mm 2.25 mm top
(A)

7.50 mm 5.50 mm 4.75 mm 2.25 mm    2.50 mm bottom
(B)

Helix pitch = 1.00 mm
Pipe diameter = 0.50 mm
Screw of 5 turns 5.00 mm 6.00 mm 2.00 mm 380a 382a

372

386

11.00 mm side
(C)

370a

Chamfer = 1.00 mm

388

R = 0.25 mm

384 conforms to the Cover
Piece base surface

382a

380a

372

386

Ø = 6.00 mm bottom
(B)

Ø = 10.00 mm
Ø = 9.00 mm
Ø = 7.50 mm top
(A)

5.50 mm

398

396

Helix pitch = 1.00 mm
Pipe diameter = 0.625 mm
Screw of 5 turns side
(C)

376

394

398

376

396

390

392

900

10.00 mm 10.00 mm 6.00 mm 6.00 mm

R = 1.00 mm

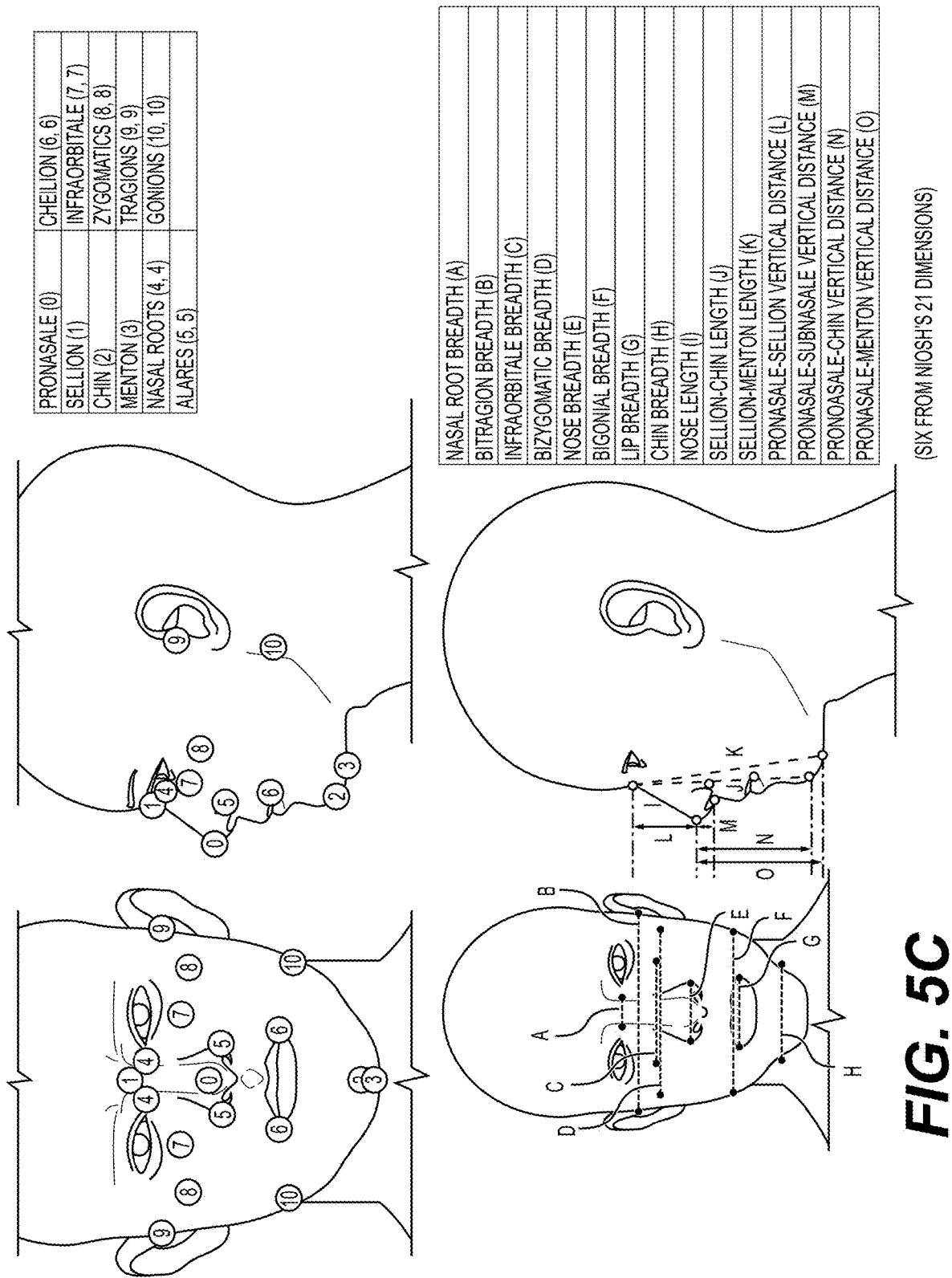

| PRONASALE (0) | CHEILION (6, 6) |
|---|---|
| SELLION (1) | INFRAORBITALE (7, 7) |
| CHIN (2) | ZYGOMATICS (8, 8) |
| MENTON (3) | TRAGIONS (9, 9) |
| NASAL ROOTS (4, 4) | GONIONS (10, 10) |
| ALARES (5, 5) | |

NASAL ROOT BREADTH (A)
BITRAGION BREADTH (B)
INFRAORBITALE BREADTH (C)
BIZYGOMATIC BREADTH (D)
NOSE BREADTH (E)
BIGONIAL BREADTH (F)
LIP BREADTH (G)
CHIN BREADTH (H)
NOSE LENGTH (I)
SELLION-CHIN LENGTH (J)
SELLION-MENTON LENGTH (K)
PRONASALE-SELLION VERTICAL DISTANCE (L)
PRONASALE-SUBNASALE VERTICAL DISTANCE (M)
PRONOASALE-CHIN VERTICAL DISTANCE (N)
PRONASALE-MENTON VERTICAL DISTANCE (O)

(SIX FROM NIOSH'S 21 DIMENSIONS)

*FIG. 5C*

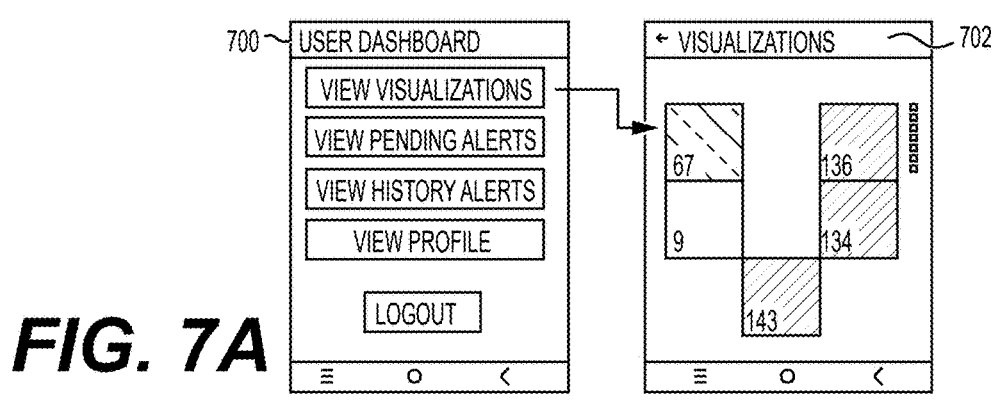

700 ~ USER DASHBOARD

VIEW VISUALIZATIONS
VIEW PENDING ALERTS
VIEW HISTORY ALERTS
VIEW PROFILE

LOGOUT

← VISUALIZATIONS ~ 702

← VISUALIZATIONS ~ 702

67
9
136
134
143

(a) LEFT AND TOP LEFT SENSORS SHOW THE PRESSURE IS LOW

← PENDING ALERTS

SENSOR: LEFT
ALERT: 2021-06-09 15:50:26
ALERT TYPE: PRESSURE
ACKNOWLEDGE ALERT ~ 704

SENSOR: TOP LEFT
ALERT: 2021-06-09 16:02:39
ALERT TYPE: PRESSURE
ACKNOWLEDGE ALERT

VIEW VISUALIZATIONS (b) LEFT AND TOP LEFT SENSORS ALERTS SHOW IN PENDING ALERTS

← ACKNOWLEDGE ALERT

ALERT FOR THE LEFT PRESSURE SENSOR

TO ACKNOWLEDGE, PLEASE MAKE SURE THE LEFT SIDE OF YOUR RPD HAS NO LEAKAGE (c) SYSTEM GENERATES ALERT TO THE USER TO ADJUST LEFT SIDE OF THE RPD

← VISUALIZATIONS 104a
104b 134
10
136
137
138

(d) LEFT TOP SENSOR IS ADJUSTED LEFT SENSOR STILL SHOWS THE PRESSURE IS LOW.

← PENDING ALERTS

SENSOR: LEFT
ALERT: 2021-06-09 15:30:26
ALERT TYPE: PRESSURE
ACKNOWLEDGMENT ALERT

VIEW VISUALIZATIONS (e) THIS ALERT SHOWS PENDING ALERTS

FIG. 7B

← VISUALIZATIONS 11
12
10
13
11

FIG. 7C

RESPIRATORY PROTECTIVE DEVICE WITH CONTINUOUS FIT MONITORING

RELATED APPLICATION

This application claims priority to, and the benefit of, U.S. Provisional Patent Application No. 63/304,893, filed Jan. 31, 2022, entitled "RESPIRATOR WITH CONTINUOUS FIT MONITORING," which is incorporated by reference herein in its entirety.

STATEMENT REGARDING FEDERALLY SPONSORED RESEARCH OR DEVELOPMENT

This invention was made with government support under Contract Number: 75D30120009567 awarded by the Centers for Disease Control and Prevention. The government has certain rights in the invention.

BACKGROUND

Workers and healthcare professionals are required to wear respiratory protective devices (RPD) in various workplaces and medical settings throughout the United States. Respiratory protective devices protect workers against insufficient oxygen environment, harmful inhalation hazards, such as dust, fog, smoke, mist, gas, vapor, spray, and biological hazards or weapons.

Respiratory protective devices protect the user in two basic ways. The first class of devices protects the user by removing contaminants from the air. This first class of devices includes particulate respirators, which filter out airborne particles, and air-purifying respirators with cartridges/canisters, which filter out chemicals, biological material, and gases. The second class of devices protects the user by supplying clean respirable air from another source. This second class of devices includes airline respirators, which use compressed air from a remote source, and self-contained breathing apparatus (SCBA), which include their own air supply.

Air-purifying respirators (APRs) can be configured with different types of filter configurations, N95, N99, N100, R95, R99, R100, P95, P99, P100, and HE. Filtering facepiece respirators (FFR) are manufactured in discrete sizes to accommodate the size, gender, and ethnic diversity in the user population when needed. The pressure exerted by a respiratory protective device, such as an N95 full-face respirator, on the face seal influences the comfort and tolerability of the user.

There is a benefit and/or a need to improve respiratory protective devices and their usage.

SUMMARY

An exemplary system and method are disclosed for a respiratory protective device configured to continuously monitor, via an integrated sensor network embedded in the device's frame, the fit or proper particulate-filtering operation of the respiratory protective device. The system can ensure proper operation of the respiratory protective device (RPD) while providing monitoring and tracking of the fit to ensure personal safety for users (e.g., healthcare professionals) wearing the device.

In some embodiments, the system can monitor, track, and aggregate the data to present via a user interface to the user. The exemplary system can provide a quantitative metric or indicator to provide a sense of security of their personal safety upon which the user can depend to know that the RPD has been donned correctly. In some embodiments, the exemplary system is customizable a user's facial features while the face flexes and moves during use.

In an aspect, a system is disclosed comprising a respiratory protective device comprising a frame having a contour that maintains a breathable filter covering over a facial region of a user, wherein the frame includes at least one sensor cavity, including a first sensor cavity (e.g., inner cavity or external cavity to the frame); a sensor network coupled to the respiratory protective device, the sensor network comprising: at least one sensor, including a first sensor, wherein the first sensor is disposed within the first sensor cavity to detect pressure or proximity of the frame at the first sensor cavity to the facial region (e.g., wherein the first sensor is configured to detect pressure, proximity, capacitance); and a signal processing module in operative communication with the at least one sensor (e.g., wired or wireless), the signal processing module configured to continuously detect the pressure or proximity of the frame at the first sensor cavity to the facial region for monitoring fit or particulate-filtering operation of the respiratory protective device (e.g., transmit pressure, proximity, capacitance signals or values to a controller, e.g., a single board computer).

In some embodiments, the signal processing module includes a communication interface configured to wirelessly communicate with a controller, wherein the controller is configured to (i) receive the pressure values, (ii) generate a notification based on the pressure values, and (iii) relay the notification to activate one of a display on a user interface, an audio device, or a haptic device.

In some embodiments, the at least one sensor cavity includes a second sensor cavity, wherein the at least one sensor includes a second sensor, and wherein the second sensor is disposed within the second sensor cavity to detect pressure or proximity of the frame at the second sensor cavity to the facial region (e.g., wherein the second sensor is configured to detect pressure, proximity, capacitance).

In some embodiments, at least one sensor is placed at a derived point on a user's facial anatomy, wherein the frame has the contour and the first sensor cavity over, or in proximity to, at least one of: an infraorbitale facial region, a zygomatic facial region, or a region therebetween; a chin point facial region, a gonion facial region, or a region therebetween; or a menton facial region, a sagittal plane, or a region therebetween.

In some embodiments, the first sensor is configured to detect pressure between the user's face and the frame.

In some embodiments, the first sensor is configured to detect temperature or liquid.

In some embodiments, the breathable filter covering comprises a replaceable filter with a pre-defined filtration configuration (e.g., a pre-defined particulate filtration efficiency).

In some embodiments, the pre-defined filtration configuration includes a particulate filtration efficiency of 95% or greater.

In some embodiments, the frame comprises a first frame portion (e.g., base frame portion) and a second frame portion (e.g., covering piece for the base frame or another base frame), the first frame portion being couplable to the second frame portion to form the contour that maintains the breathable filter covering over the facial region and the first sensor cavity in proximity to the facial region.

In some embodiments, the frame is a unitary body (e.g., a single piece or attached to form a single body).

In some embodiments, the system further includes a set of interlocking screws, including a first screw and a second screw, wherein the first screw is configured to be attached to a screw recess (e.g., the interlocking holes) located in the frame to couple the first frame portion to the second frame portion and maintain the breathable filter covering in the contour of the frame.

In some embodiments, at least one sensor is at least one of (i) fabric-based (e.g., woven or knitted conductive fabrics), (ii) conductive material printed on a substrate comprising a textile fabric, a polyimide (PI) film, a polyethylene terephthalate (PET) film, or a polyacrylic acid (PAA) film.

In some embodiments, the at least one sensor is coupled to the signal processing module over a conductive material comprising fiber, yarn, film, or wire.

In some embodiments, the controller comprises a speaker (e.g., to generate an audible output), a light source (e.g., LED), or a piezoelectric transducer (e.g., to generate a vibration).

In some embodiments, the first sensor is located at a chin position, the second and a third sensors are located on a mid-cheek position, and a fourth and a fifth sensors are located on an upper-cheek position, or a combination thereof.

In some embodiments, the controller is configured to output pressure values of the one or more sensors to a monitoring application (e.g., APP on a smart phone, smart device, computer, or site safety monitoring office).

In some embodiments, the system further comprises a fastening hub comprising fastening hooks and attachable straps.

In another aspect, a method of monitoring fit of a respiratory protective device is disclosed, the method comprising: providing a respiratory protective device comprising: a frame (e.g., 3D printed or conventionally manufactured) having a contour that maintains a breathable filter covering over a facial region of a user, wherein the frame includes at least one sensor cavity, including a first sensor cavity (e.g., inner cavity or external cavity to the frame); and a sensor network coupled to the respiratory protective device, the sensor network comprising (i) at least one sensor, including a first sensor, wherein the first sensor is disposed within the first sensor cavity to detect pressure or proximity of the frame at the first sensor cavity to the facial region (e.g., wherein the first sensor is configured to detect pressure, proximity, capacitance); and (ii) a signal processing module in operative communication with the at least one sensor (e.g., wired or wireless), the signal processing module configured to continuously detect the pressure or proximity of the frame at the first sensor cavity to the facial region for monitoring fit or particulate-filtering operation of the respiratory protective device (e.g., transmit pressure, proximity, capacitance signals or values to a controller, e.g., a single board computer); continuously monitoring signal or derived values produced by the first sensor; and providing the signal or derived value to a controller for display or alert generation.

In some embodiments, the respiratory protective device is fabricated by: 3D printing the frame for the respiratory protective device; placing/installing the first sensor in the first sensor cavity; and connecting the first sensor to the signal processing module.

In some embodiments, the method further includes: producing an alert signal when at least one signal or derived value is outside of a predetermined range (e.g., pressure extends above or below a preset threshold); and producing a removal signal to remove the alert signal when the at least one signal or derived value returns to the predetermined range (e.g., user fixes the RPD and pressure values return to the expected/permissible range).

In some embodiments, the method further includes generating an alert when at least one signal or derived value falls below a threshold value (e.g., pressure drops too low).

In some embodiments, the method further includes relaying the generated alert to one of a user interface for displaying the signals or derived values, an audio device for playing sounds based on the signals or derived values, or a haptic device for causing vibrations based on the signals or derived values.

In some embodiments, the method further includes producing a removal signal to remove the alert signal when the at least one signal or derived value returns to the predetermined range. (e.g., the user fixes the RPD, and pressure values return to the expected/permissible range).

In another aspect, a system is disclosed comprising computing devices (e.g., back-end servers) configured to operate with a respiratory protective device, wherein the computing devices are configured to continuous monitor fit of the respiratory protective device on a user, wherein the respiratory protective device includes a frame having the contour that maintains a breathable filter covering over a facial region of a user, wherein the frame includes at least one sensor cavity, including a first sensor cavity (e.g., inner cavity or external cavity to the frame), wherein the frame is configured to house a sensor network coupled to the respiratory protective device, the sensor network comprising (i) at least one sensor, including a first sensor, wherein the first sensor is disposed within the first sensor cavity to detect pressure or proximity of the frame at the first sensor cavity to the facial region (e.g., wherein the first sensor is configured to detect pressure, proximity, capacitance); and (ii) a signal processing module in operative communication with the at least one sensor (e.g., wired or wireless), the signal processing module configured to continuously detect the pressure or proximity of the frame at the first sensor cavity to the facial region for monitoring fit or particulate-filtering operation of the respiratory protective device (e.g., transmit pressure, proximity, capacitance signals or values to a controller, e.g., a single board computer).

BRIEF DESCRIPTION OF DRAWINGS

The skilled person in the art will understand that the drawings described below are for illustration purposes only.

FIGS. 5A-5E illustrate an example method to generate a customized respiratory protective device from a model, according to one or more implementations.

FIGS. 7A-7C each shows an example user interface for monitoring the fit of a sensor-integrated respiratory protective device (RPD) or customizable device, according to one implementation.

DETAILED DESCRIPTION

Each and every feature described herein, and each and every combination of two or more of such features, is included within the scope of the present disclosure, provided that the features included in such a combination are not mutually inconsistent.

The citation and/or discussion of such references is provided merely to clarify the description of the present disclosure and is not an admission that any such reference is "prior art" to any aspects of the present disclosure described herein. In terms of notation, "[n]" corresponds to the nth references in the list. All references cited and discussed in this specification are incorporated herein by reference and to the same extent as if each reference was individually incorporated by reference.

Example System #1

Figure 1A:
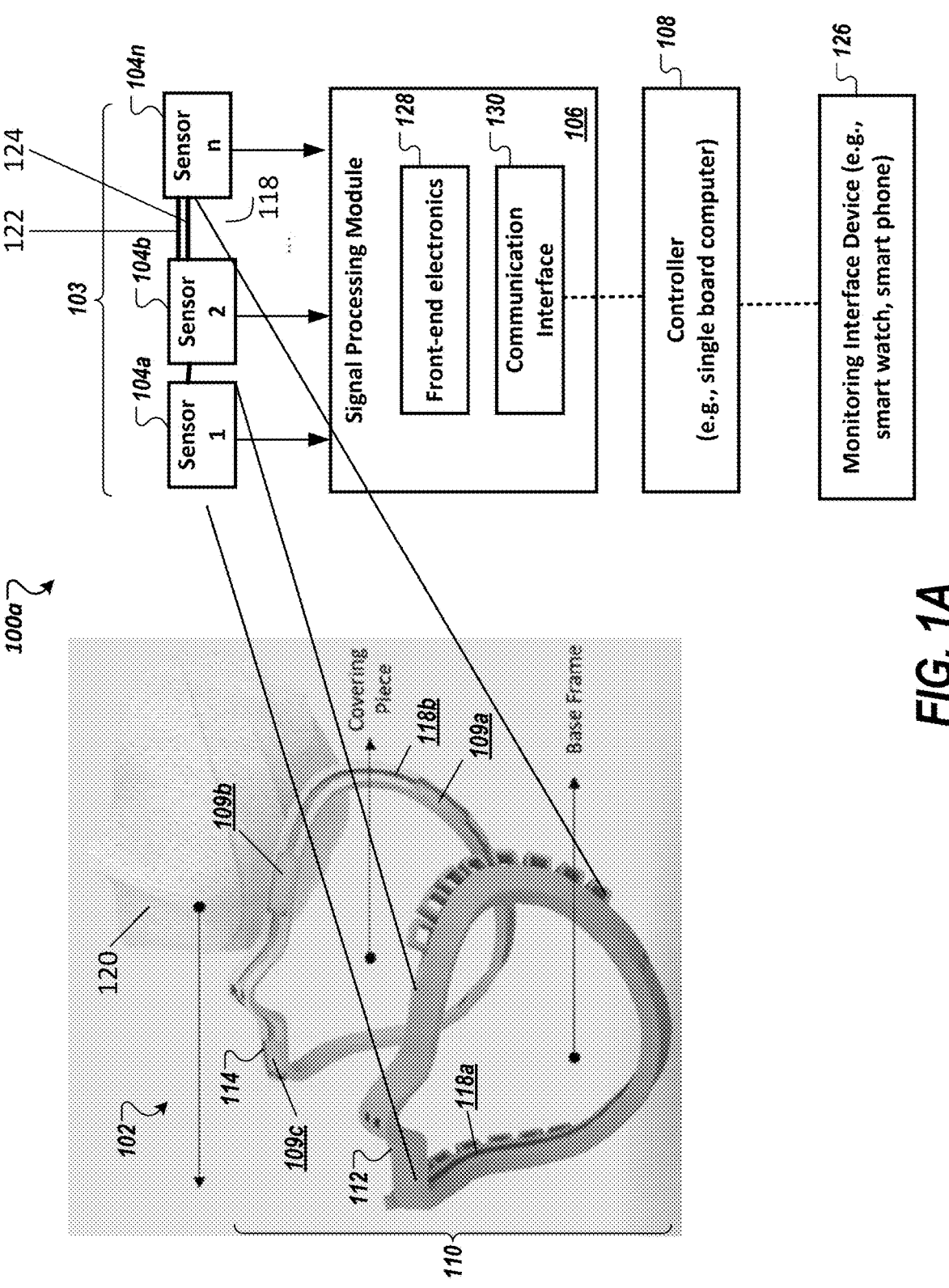
FIGS. 1A and 1B each illustrate an example of a continuous fit monitoring system for a sensor-integrated respiratory protective device (RPD) or customizable device of the same, in accordance with an illustrative embodiment.
Figure 1B:
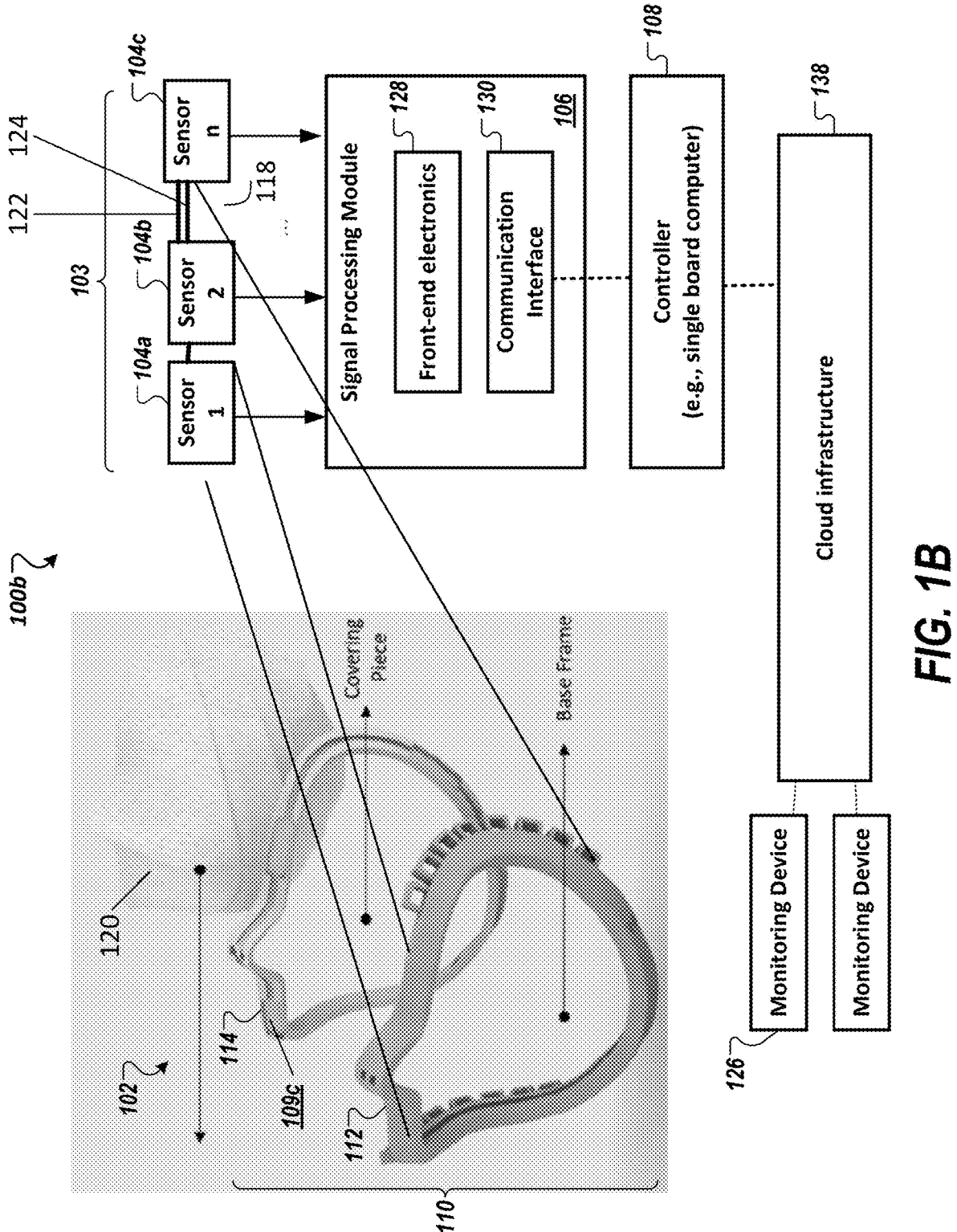

FIGS. 1A and 1B each illustrate an example of a continuous fit monitoring system 100 (shown as 100a, and 100b, respectively) for a sensor-integrated respiratory protective device (RPD) 102. FIG. 1A shows the continuous fit monitoring system 100a configured as a stand-alone monitoring device. FIG. 1B shows the continuous fit monitoring system 100b configured as a cloud-networked device. In the example shown in FIG. 1A, the sensor-integrated respiratory protective device includes a sensor network 103 comprising a set of one or more sensors 104 (shown as "sensor 1" 104a, "sensor 2" 104b, to "sensor n" 104n), a signal processing module 106, and a controller 108.

Referring to FIG. 1A, the respiratory protective device 102 includes a frame 110 (e.g., custom fit or otherwise as described herein) comprising a first portion 112 (shown as a "base frame") and second portion 114 (shown as a "covering piece") that, when joined, collectively forms a contour over a person's face to ensure a fit to the user's facial structure. In some embodiments, the frame 110 can be implemented as a single unitary structure.

The respiratory protective device 102 includes a breathable filter 120 configured to filter particulates from the air. In some implementations, the breathable filter 120 is a replaceable filter with a pre-defined filtration configuration having a desired particulate filtration efficiency. In some implementations, the desired particulate filtration efficiency is 95% or greater (e.g., an N95 or P100 mask filtration). Other filter configurations may be used, e.g., N95, N99, N100, R95, R99, R100, P95, P99, P100, HE, among others described herein.

In the example shown in FIG. 1A, the frame 110 includes a number of cavities 109 (shown as 109a-109c and additionally 109d and 109e in FIGS. 3A-D) for a number of sensors 104 (e.g., 104a-104n). In some embodiments, the cavities 109 and sensors 104 may be disposed along the frame 110 at a position that corresponds to an infraorbitale facial region, a zygomatic facial region, or a region therebetween; a chin point facial region, a gonion facial region, or a region therebetween; or a menton facial region, a sagittal plane, or a region therebetween.

In some embodiments, the respiratory protective device 102 includes conduits 118 to house electrical connections (e.g., wiring) between the sensor network 103 and the controller 108 configured with a local datastore 135 (see FIG. 2) to store the measured signal. In other embodiments, the sensors may be connected by wireless connection or via surface conductive paint. In the example shown in FIG. 1, each of the base frame 112 and the covering piece 114 form network channels (shown as 117a, 117b) to house the sensor network 103. In other implementations, a different number of sensors 104a-n are used (e.g., one or two sensors). While in the example of FIG. 1A, the frame 110 includes both a first portion 112 and a second portion 114 coupled together, in other implementations, the frame can be made unitary. In some implementations, the sensors 104a-n can be made from woven or knitted conductive fabrics. In some implementations, the data buses 118 may be implemented using conductive yarns or printed using conductive material on PI/PET film or copper wire. In some implementations, the sensors 104a-n and data buses 118 can be printed using conductive materials on any substrate, such as polyimide (PI) film, polyethylene terephthalate (PET) film, polyacrylic acid (PAA), textile fabric, among others.

The signal processing module 106 is disposed on the respiratory protective device 102 in a location outside of the inner conduit of the frame 110. The signal processing module 106 includes front-end electronics 128 and a communication interface 130. The signal processing module 106 receives signals (e.g., analog pressure signals) from the sensor network 103 along the data bus/conduit 118 and performs an analog-to-digital conversion (ADC). For example, the front-end electronics 128 may receive the signals and perform the ADC.

The signal processing module 106 in system 100a is in wireless communication with a controller 108 (e.g., a single-board computer). The communication interface 130 relays signals to the controller 108. The wireless communication in system 100a between the communication interface 130 and the controller 108 is accomplished by Bluetooth antenna. In other implementations, the communication may be accomplished by WiFi or any other common wireless transmission means. In system 100a, the controller 108 is part of the respiratory protective device 102, for example, located on a portion of the frame 110 separate from the signal processing module 108. In some implementations, the controller 108 is disposed on a portion of a hub connected to the frame 110 and located on the back of the user's head.

The controller 108 processes the measured signals (i) to locally monitor for fit (i.e., that the measured signals are within the pre-defined thresholds or ranges) and (ii) to relay the signals to a monitoring interface device 126 (e.g., a smart device, a wearable technology, smart watch, or smart phone). When an alert is generated, the controller 108 may then provide the alerts to the monitoring interface device 126. The monitoring interface device 126 can then store the measured signals and provide an interface for a notification of the alert and for a query of historical data. The monitoring interface device 126 may also display or generate a notification through its audio device, vibratory, or haptic output. FIG. 7A shows an example of the measured signal being presented as a heat map visualization.

Example System #2

Figure 2:
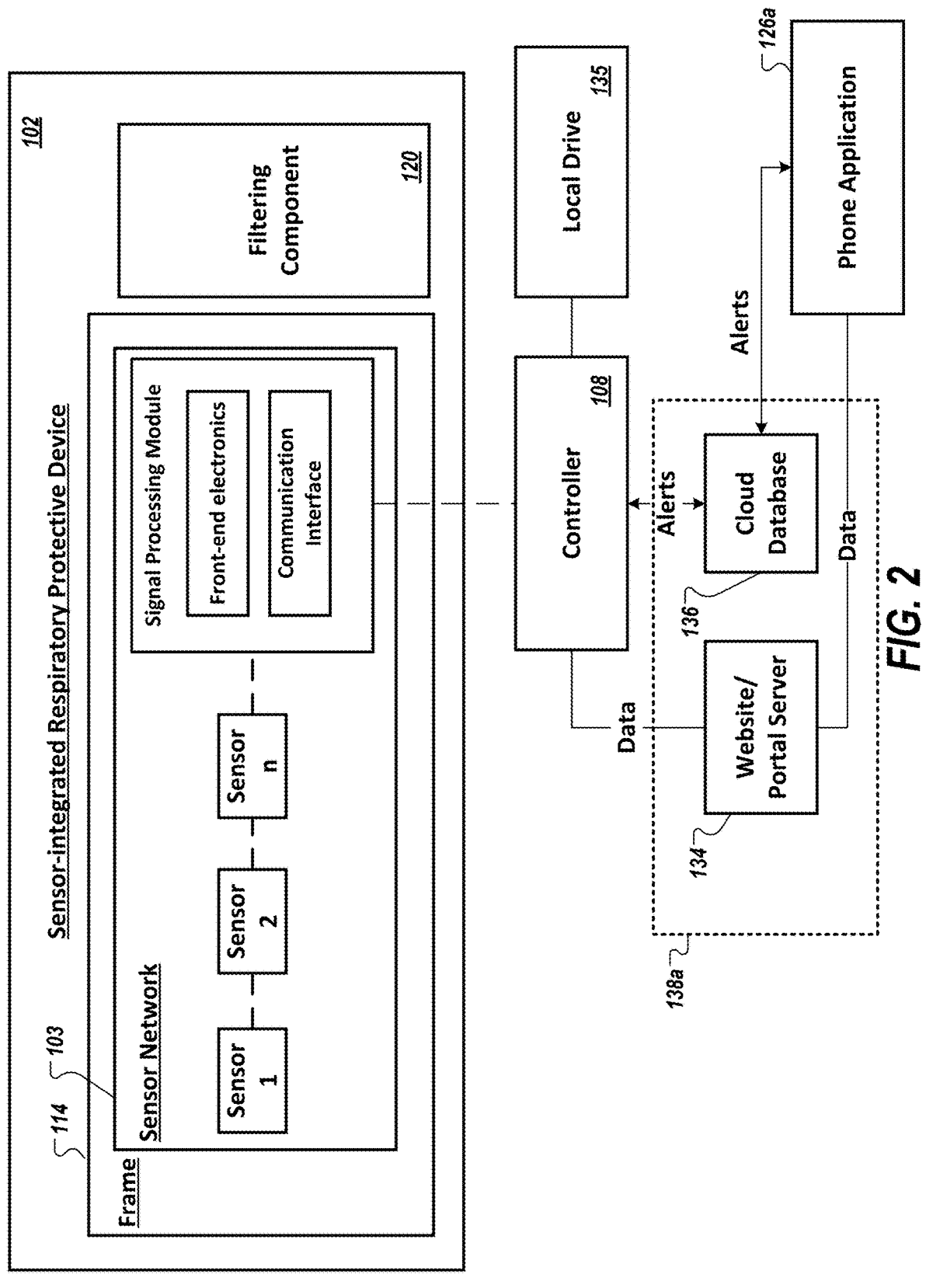
FIG. 2 is a diagram showing an example implementation of a continuous fit monitoring system of FIG. 1 or 2, according to one implementation.

FIG. 1B shows the continuous fit monitoring system 100b configured as a cloud-networked device that interfaces with cloud infrastructure 138. The cloud infrastructure 138 can also receive and store the measured signals and/or provide curation capabilities for an interface for the notification of the alert and for the query of historical data. FIG. 2 is a diagram showing an example architecture of the cloud infrastructure 138 that can interface with the continuous fit monitoring system 100 in accordance with an illustrative embodiment.

In the example shown in FIG. 2, the cloud infrastructure 138 (shown as 138a) includes a web hosting capability 134 (shown as "Website/Portal Server" 134) and a cloud database 136.

Each of the website/server 134 and the cloud database 138 can communicate with a monitoring interface device 126 (shown as "Phone Application" 126a).

Example Sensor-Integrated Respiratory Protective Device #1

Figure 3A:
FIGS. 3A-3T are diagrams of example mechanical designs of components of a sensor-integrated respiratory protective device configured for continuous fit monitoring, e.g., of FIG. 1 or 2, according to various implementations.
Figure 3B:
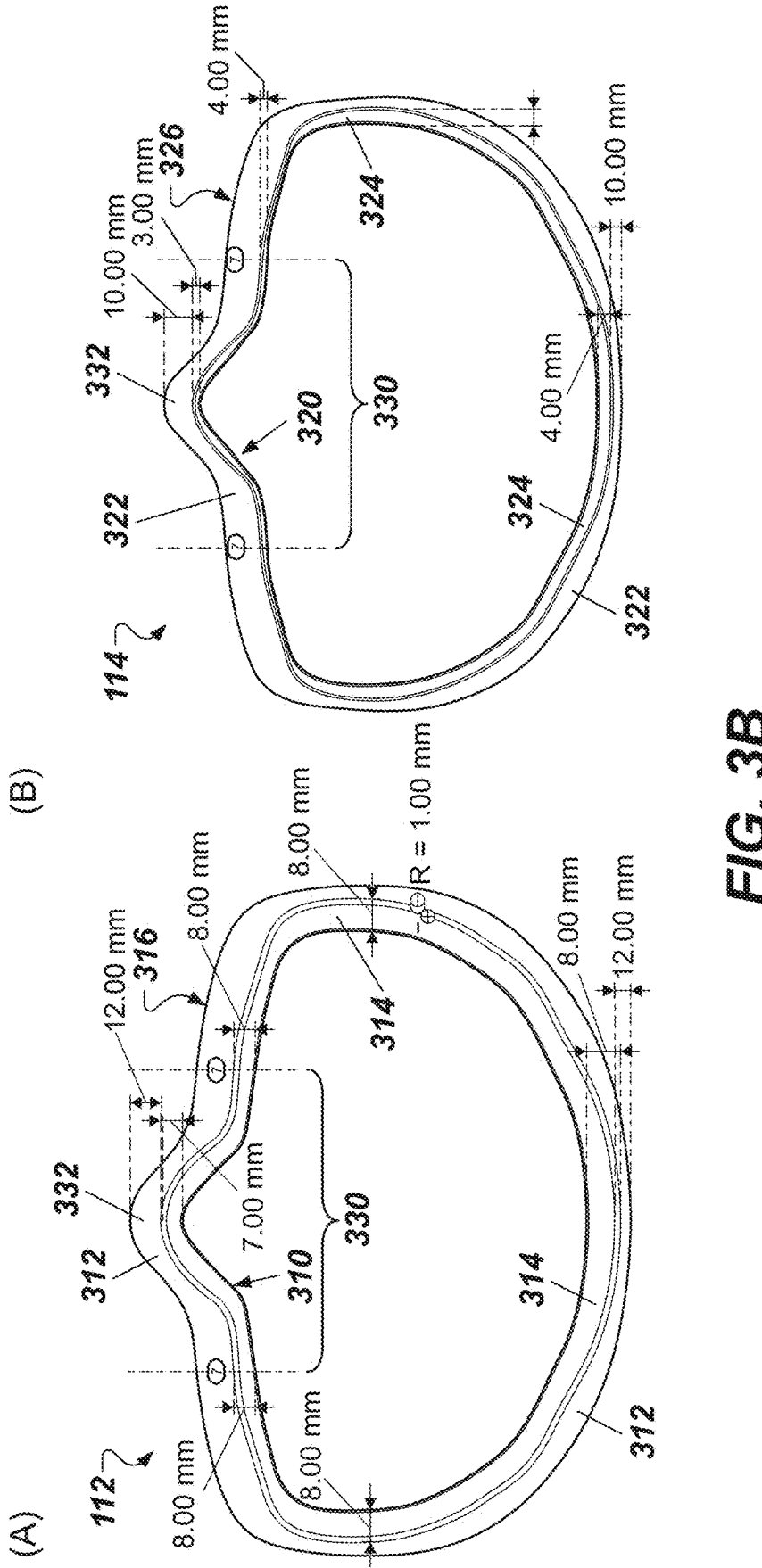
Figures 3C, 3D:
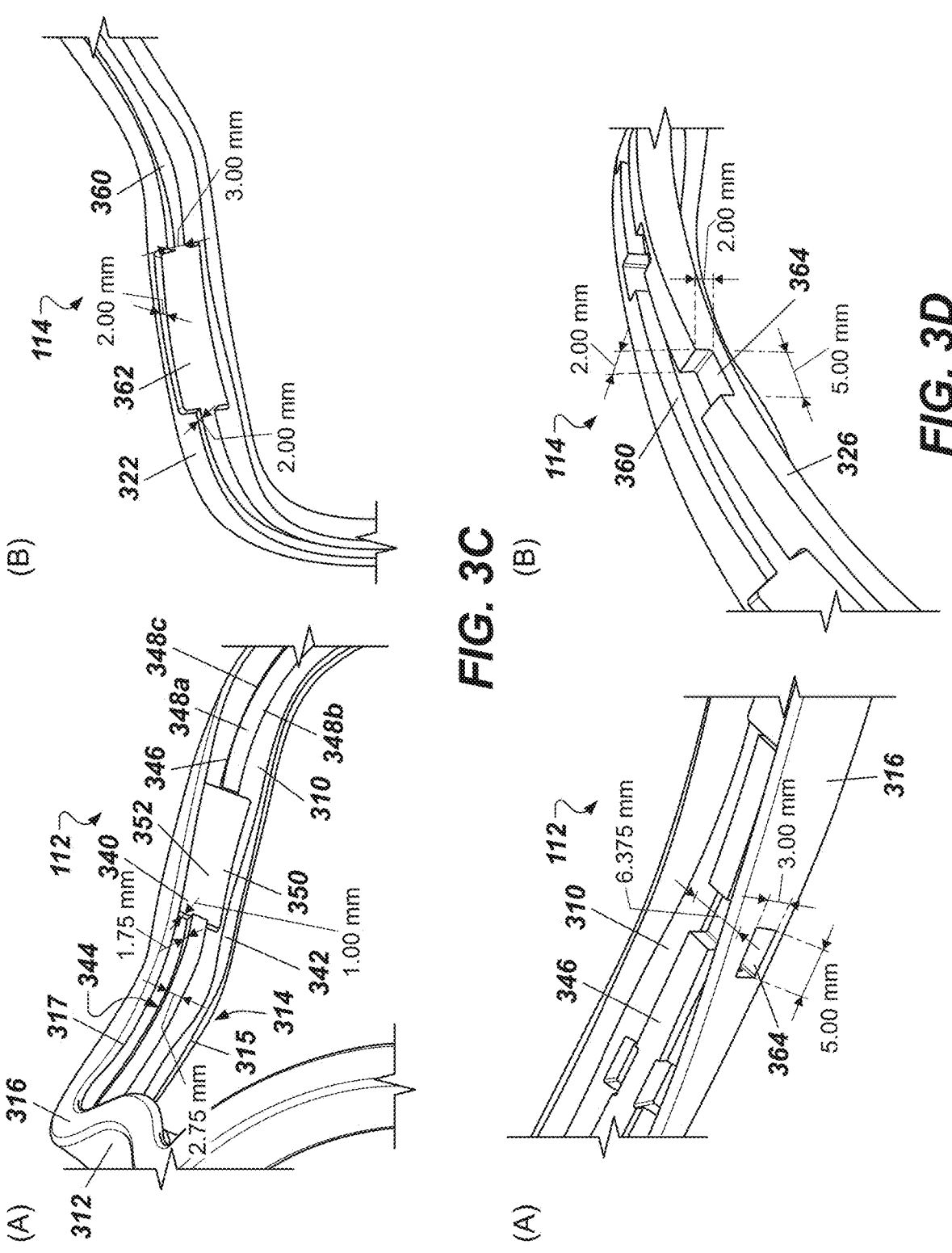
Figure 3E:
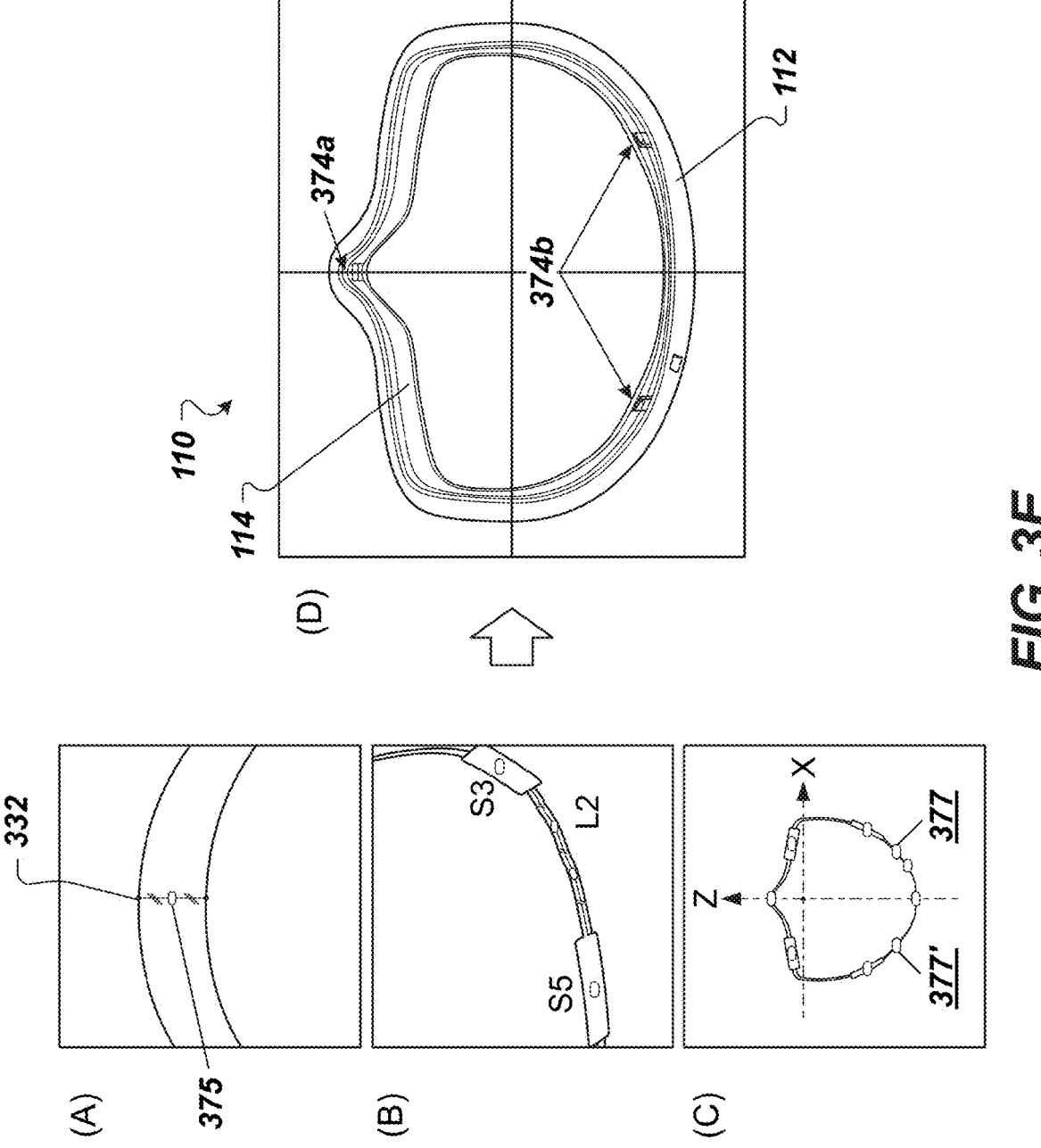
Figure 3F:
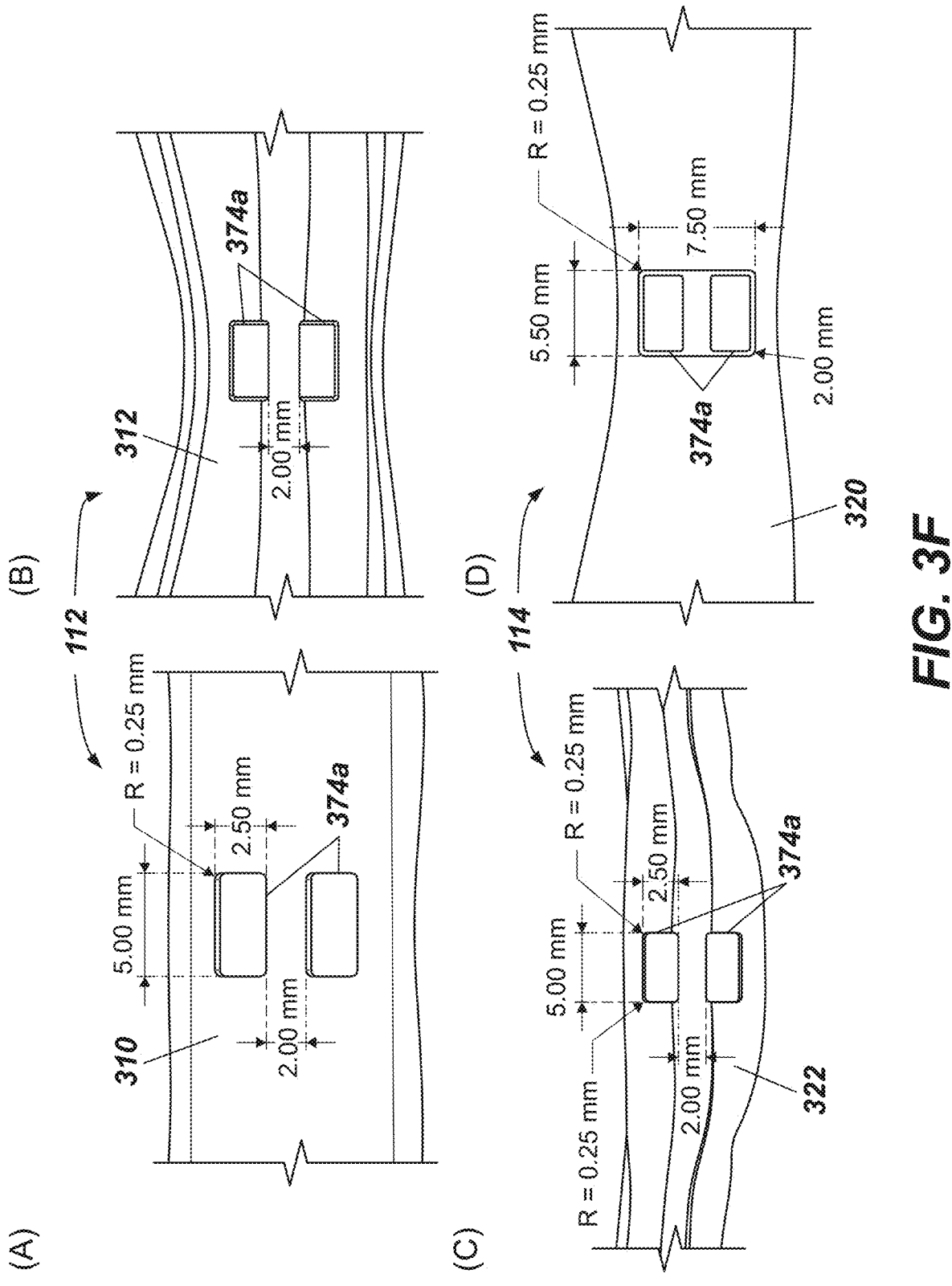
Figure 3G:
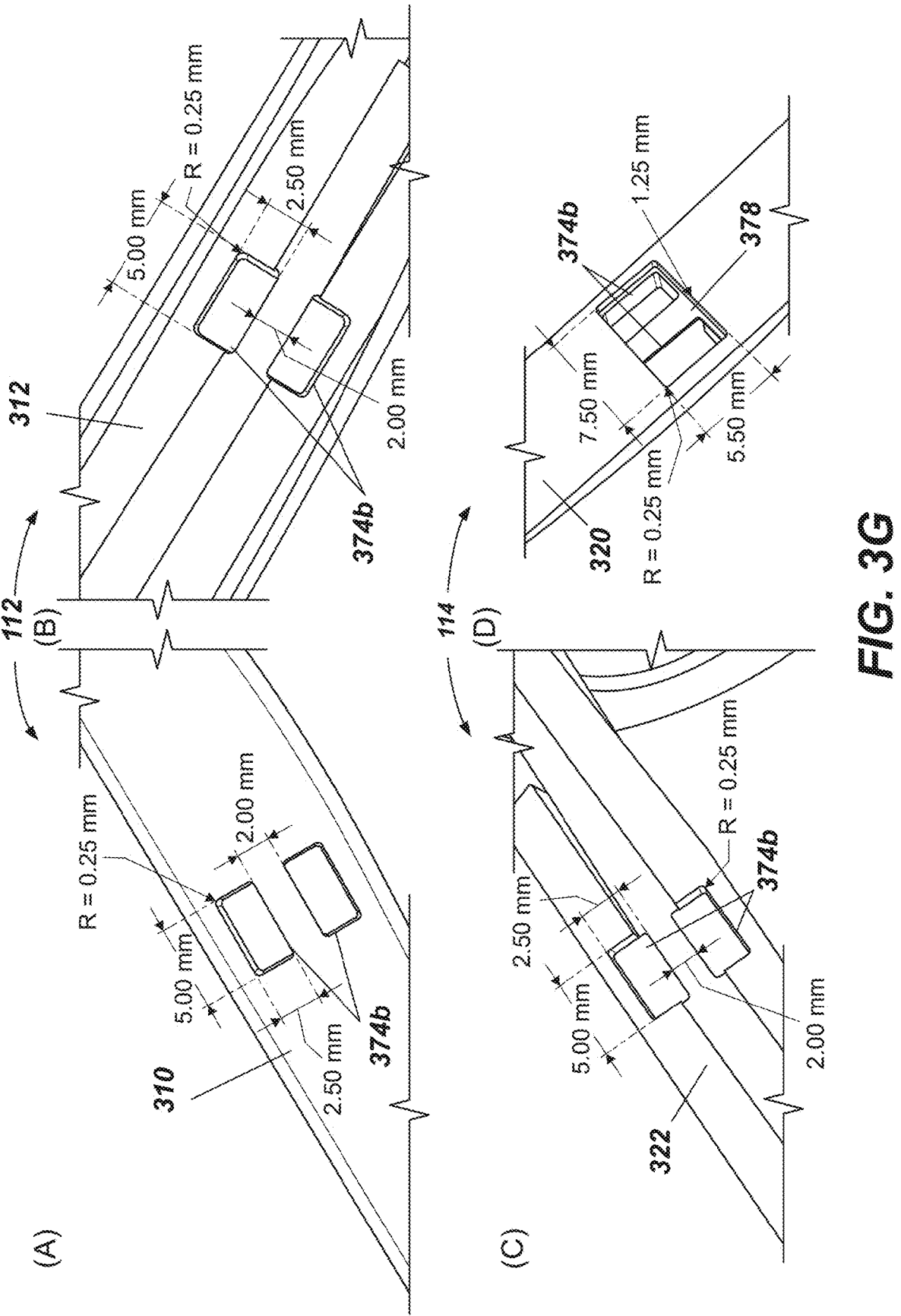
Figures 3H, 3I:
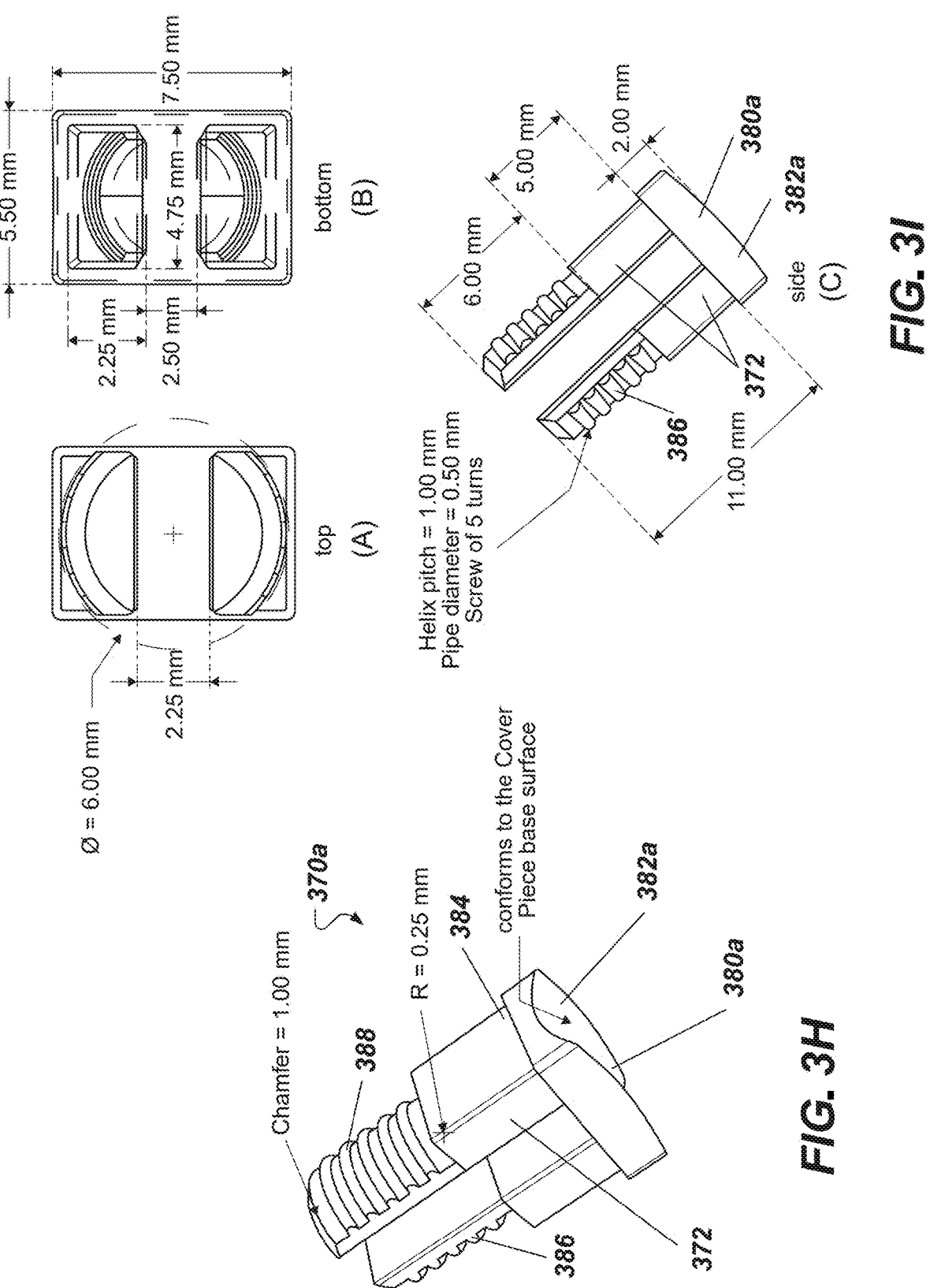
Figures 3J, 3K:
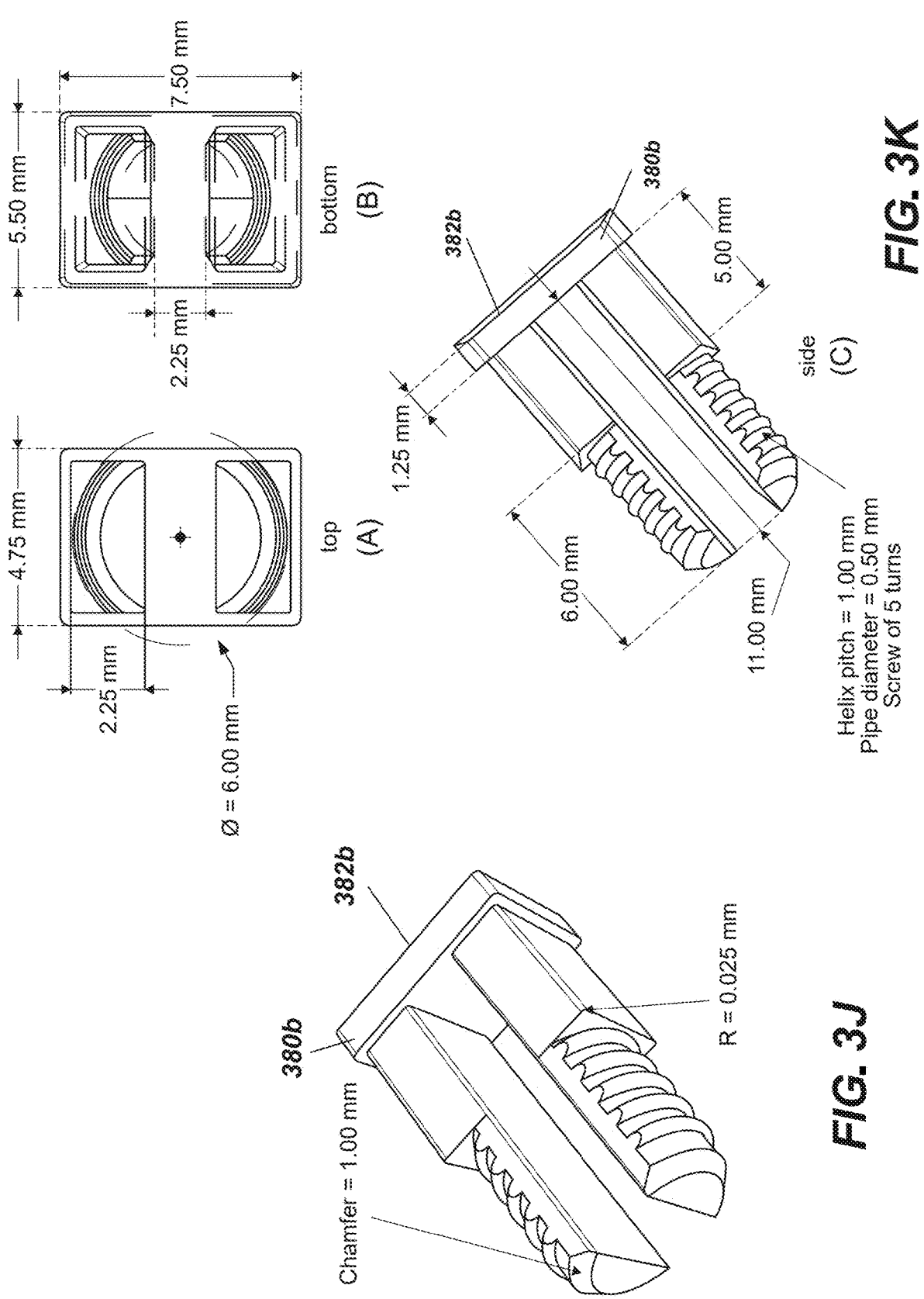
Figures 3L, 3M:
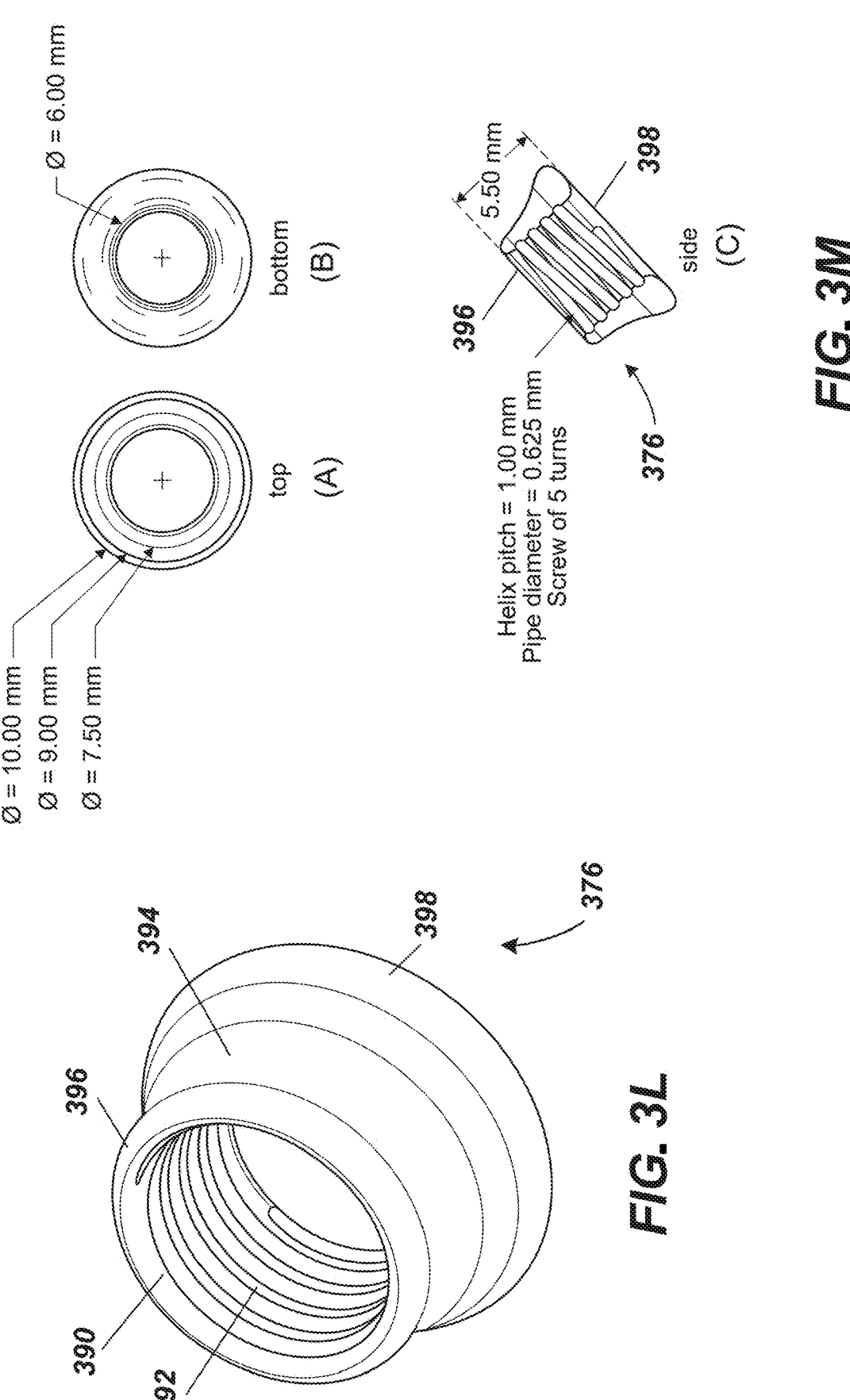
Figure 3O:
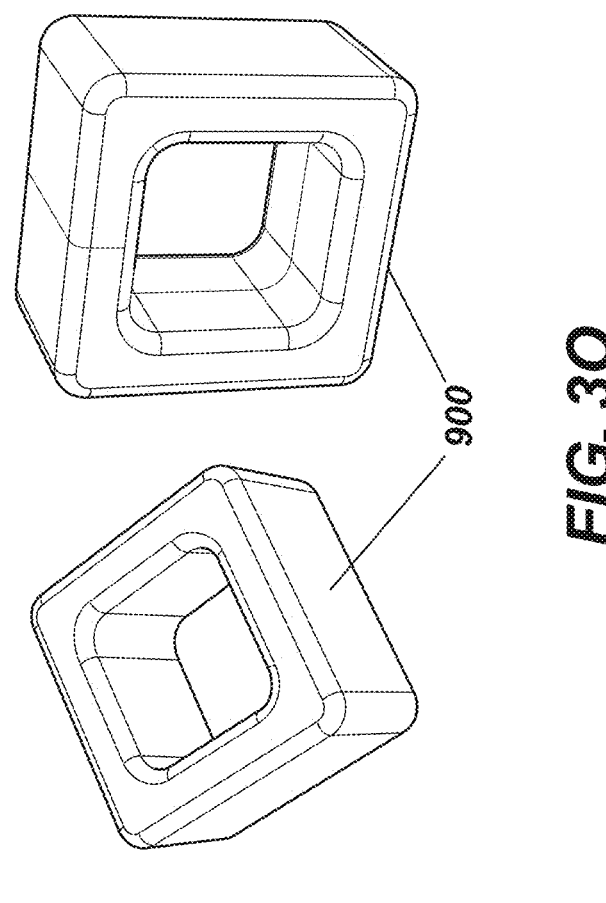
Figure 3N:
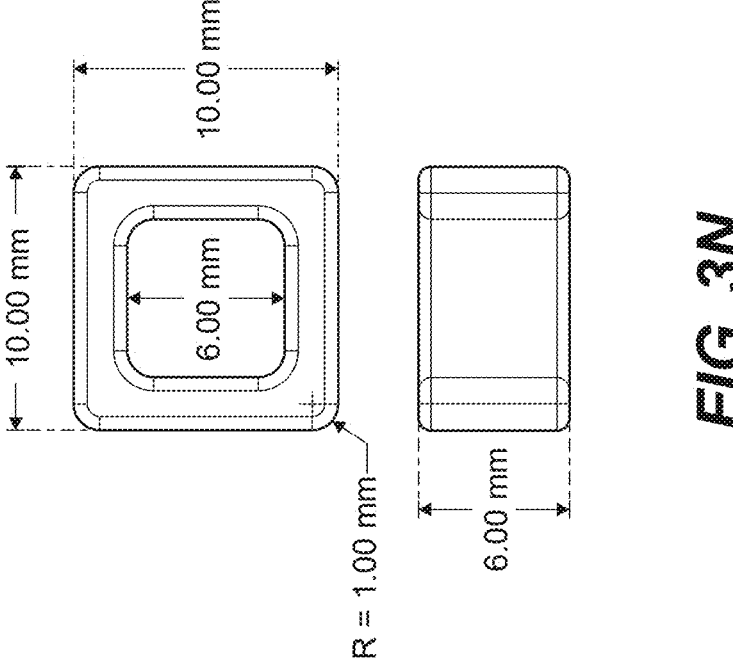
Figures 3P, 3Q:
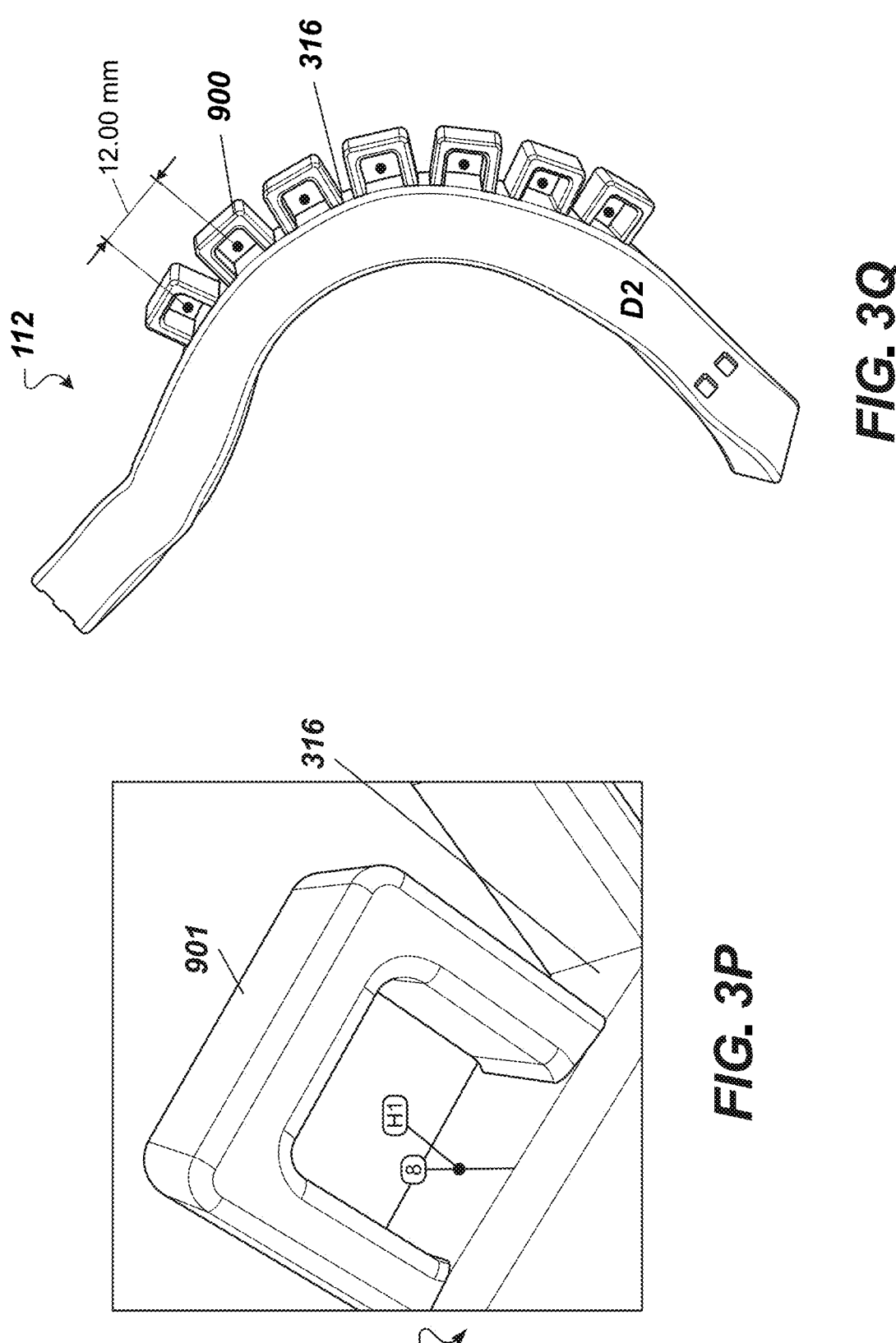
Figures 3R, 3S:
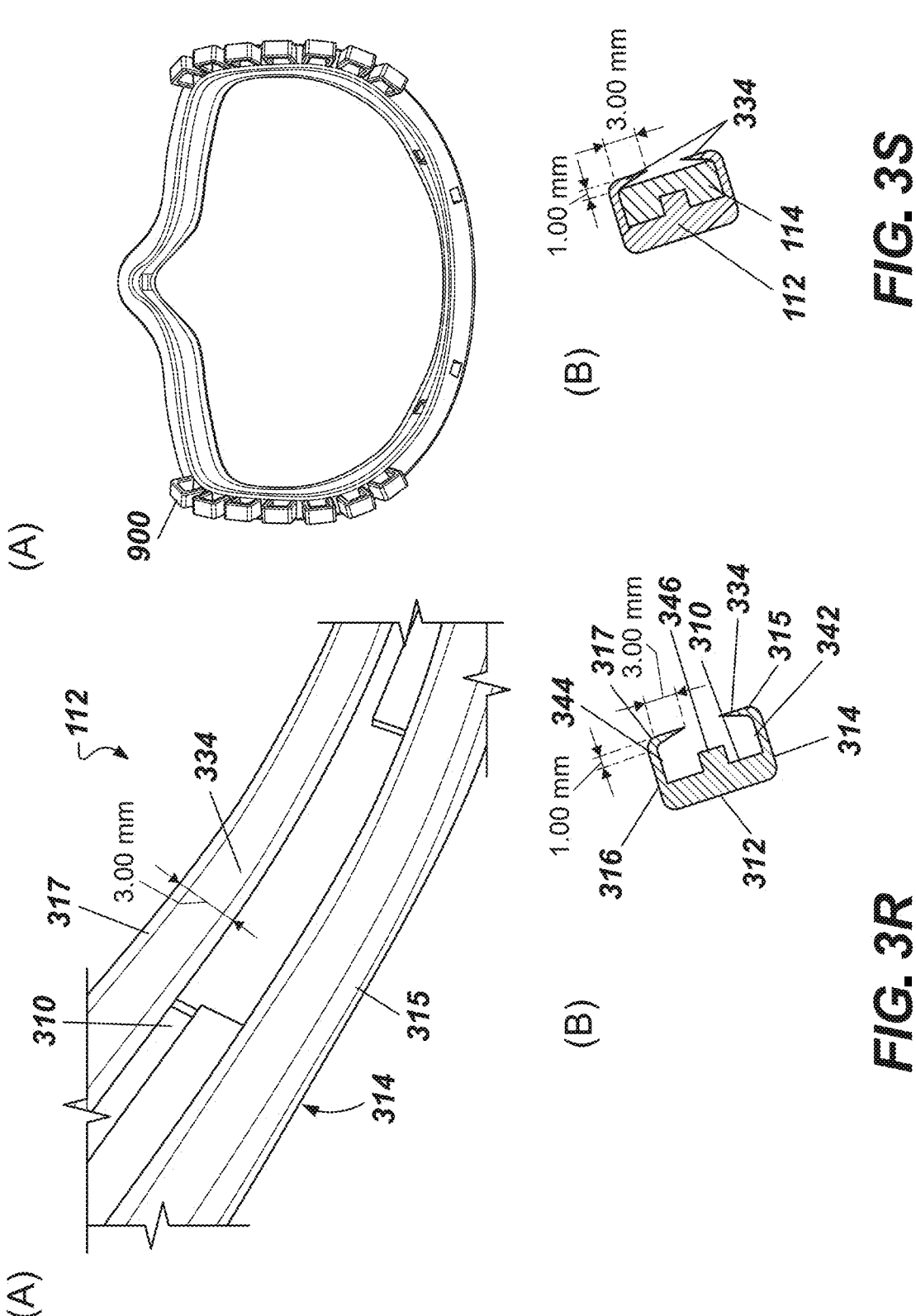
Figure 3T:
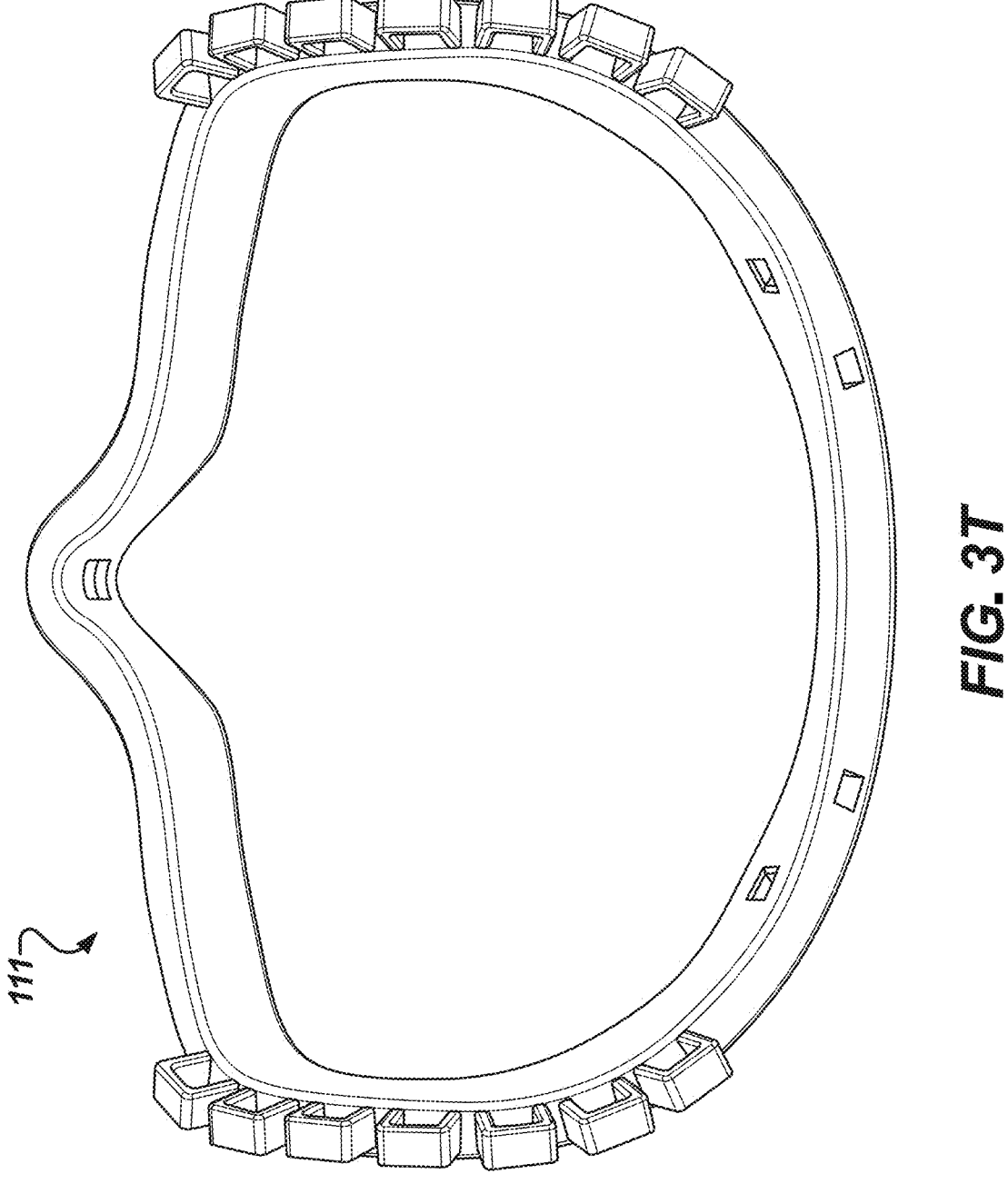

FIGS. 3A-3T are diagrams of examples of mechanical designs of various components and examples of processes to design the same of a sensor-integrated respiratory protective device configured for continuous fit monitoring, e.g., of FIG. 1 or 2, according to various implementations. FIG. 3A shows an implementation of the components and their integrations to form the sensor-integrated respiratory protective device. FIGS. 3B, 3C, and 3D show details of the frame. FIGS. 3E-3G show details on the screw holes. FIGS. 3H-3M show details on the screws and screw cap. FIGS. 3N-3Q show details on the fastening hook that may be integrated into the device. FIGS. 3R and 3S shows details on frame construction and design. FIG. 3T shows a second embodiment of the sensor-integrated respiratory protective device as a single unitary structure.

System Design. FIG. 3A shows an implementation of the components and their integrations to form the sensor-integrated respiratory protective device. Like numbering between FIGS. 3A-3T (as well as other figures) represent like-elements to those shown in other figures within this document. In the example shown in FIG. 3A, the frame 110 comprises two components: a base frame 112 and a covering piece 114 that can be separately manufactured and embedded with the sensors and electronics (shown collectively as 103) prior to final assembly. The construction includes a set of re-attachable screw sets 370 that can facilitate the quick removable and attachment of the breathable filter while maintaining the seal for the highest level of respiratory protection level when desired. The frame 110 may be readily manufactured to provide customized face wear and protection for the user or may be manufactured for different facial shapes and sizes to be fitted for the person.

Frame. FIGS. 3B, 3C, and 3D show details of the frame 110 formed of the base frame 112 and covering piece 114. In FIG. 3B, the base frame 112 shown in subpanel (A) includes a base inner surface 310, as the back of the component, that would mate with the covering piece 114, shown in subpanel (B). The base outer surface 312, as the front of the component, forms the outer surface of the frame 110 and the device 102 in the final assembled form. The base inner surface 310 and base outer surface 312 are substantially parallel to the face surface.

The base frame 112 includes a first base surface 314 that forms an interior side of the base frame, located between the base inner surface 310 and the base outer surface 312 (e.g., closer to a filtering component to be placed at the center of the base frame 112). The base frame 112 includes a second base surface 316 (see FIG. 3D) located opposite and spaced apart from the first base surface 314, extending between the base outer surface 312 and the base inner surface 310 on an exterior side of the base frame 112 (e.g., further away from the center of the base frame 112). In other words, the first base surface 314 and the second base surface 316 can be viewed as extending out from a user's face and are substantially perpendicular to the face surface.

The covering piece 114 includes a structure having a corresponding shape to that of the base frame 112 and includes (i) a cover inner surface 320 to be placed in contact with the user's face and (ii) a cover outer surface 322 to mate with the base frame 112 and the base inner surface 310. Both the cover inner surface 320 and the cover outer surface 322 can be characterized as being substantially parallel to the face surface. The covering piece 114 includes (iii) a first cover surface 324 that connects between the cover inner surface 320 and the cover outer surface 322 on an interior side of the covering piece 114 (e.g., closer to a filtering component in the center of the base frame 112) and (iv) a second cover surface 326 located opposite and spaced apart from the first cover surface 324, extending between the cover outer surface 322 and the cover inner surface 320 on an exterior side of the covering piece 114 (e.g., further away from the center of the base frame 112). The first cover surface 324 and the second cover surface 326 can be characterized as extending out from a user's face by being substantially perpendicular to the face surface.

The base frame 112 and covering piece 114 each include a nose bridge area 330 that is intended to seat and extend from (i) the infraorbitale (marked as point "7" in FIG. 3B) of the user's face to (ii) the center nose bridge apex 332 of the nose bridge area 330. The nose bridge area 330 includes contours forming an angle converging at a nose bridge apex 332 at the center of the nose bridge area 330.

The depth of the base frame 112, in this design, as measured across the first base surface 314 is 8 mm (essentially defining the depth the base frame 112 would extend from a user's face). At the nose bridge area 330, the depth of the base frame 112 is reduced to 7 mm to reduce the weight and footprint of the base frame 112. The thickness (e.g., outer surface width) of the base frame 112, as measured across the base outer surface 312 is 12 mm (the distance between the first base surface 314 and the second base surface 316). Each of the surface junctions of the base frame 112 has a fillet radius of 1 mm.

The depth of the covering piece 114, in this design, as measured across the first cover surface 324 is 4 mm (essentially defining the depth the covering piece 114 would "stick out" from a user's face). At the nose bridge area 330, the depth of the covering piece 114 is reduced to 3 mm to reduce the weight and footprint. The thickness of the covering piece 114, as measured across the cover outer surface 322, is 10 mm (the distance between the first cover surface 324 and the second cover surface 326). The smaller thickness of 10 mm for the covering piece 114 allows the covering piece 114 to fit snugly into the base frame 112.

Referring to FIGS. 3C and 3D, base frame 112 and covering piece 114 includes network channels 117a, 117b for integration of the sensor network 103. The base frame 12 includes extrusions while the covering piece 114 includes corresponding slots that can (i) facilitate frictional fitting between the two pieces to maintain their attachments during the fabrication of the frame 110 and (ii) accommodate the sensors 104a-104n and their associated data buses or conduit 118. The extrusions and slots may be dimensions to form cavities for the electronics and sensors when the base frame 112 and covering piece 114 are assembled.

In this design, each sensor 104a-104n of the sensor network 103 is disposed close to the covering piece side of the frame 110 and is configured to acquire measurement signals (e.g., pressure, contact, capacitance, or other properties as described herein) to determine such properties at the interface between the user's facial structure and the frame 102. To reduce the number of wires, each sensor 104a-104n is connected to a common power line 122 (shown in FIG. 1A) that is drawn through the conduit 118 to provide power from the signal processing module 106 to each of the sensors 104a-104n. Also, each sensor 104a-104n includes a data line 124 (shown in FIG. 1A) drawn through the conduit 118 for transmitting the measured signals to the signal processing module 106 at the end of a data bus containing each of the sensor data lines 124.

FIG. 3C, subpanel (A), shows a rear view of the base frame 112, and FIG. 3C, subpanel (B), shows the front view of the covering piece 114. It can be observed from the left and right views that a portion of the base frame 112 has extrusions that match with a corresponding portion with cavities or channels of the covering piece 114. It can also be observed that the base inner surface 310 is set back from the edges of the first base surface 314 and second base surface 316 such that a third base surface 342 and fourth base surface 344 extend from the edges 315, 317 of the first and second base surfaces 314, 316 to the base inner surface 310. The third and fourth base surfaces 342, 344 are substantially parallel to the first and second base surfaces 314, 316, respectively.

It can also be observed that the base inner surface 310 includes a channel extrusion 346 centered on the base inner surface 310 between the third and fourth base surfaces 342, 344. The channel extrusion 346 includes a channel surface 348a separated and spaced apart from the base inner surface 310. In this design, the channel surface 348a is 1.75 mm from the base inner surface 310. The channel extrusion 346 includes a channel side surfaces 348b, 348c opposite and spaced apart from each other and centered about the channel extrusion 346. The channel side surfaces 348b, 348c define the width of the channel extrusion, which in this design is 2.75 mm.

It can also be observed that the base inner surface 310 includes a sensor extrusion 350 centered on the base inner surface 310 between the third and fourth base surfaces 342, 344. The sensor extrusion 350 includes a sensor extrusion surface 352 separated and spaced apart from the base inner surface 310. In this design, the sensor extrusion surface 352 is 1.00 mm from the base inner surface 310.

The cover outer surface 322 of the covering piece 114 includes corresponding slots to accommodate both the extrusions 346, 350 of the base frame 112 and the structure of the sensor network 103. The cover outer surface 322 includes slots or channels 360 to accommodate conduit 118 or wires between sensors 104a-104n. The channels 360 are centered on the cover outer surface 322 between the first and second cover surfaces 324, 326. The channels 360 have a channel depth and a channel width. In this design, the channel depth is 2 mm, and the channel width is 3 mm.

The covering piece 114 also forms a number of sensor cavities 362, on the cover outer surface 322, to accommodate the sensors 104a-104n. The sensor cavity 362 is similarly centered on the cover outer surface 322 and includes a sensor slot depth. In this embodiment, a sensor slot depth is 2.0 mm.

FIG. 3D shows details of a data bus or conduit opening 364 in each of the base frame 112 (in subpanel (A)) and the covering piece 114 (in subpanel (B)). For the sensor network 103 to receive power and transfer data, each sensor 104a-104n is connected to a data line 124 and a common power line 122 (shown in FIG. 1A). At the termination of the sensors 104a-104n, all of the lines 122, 124 form a data bus which then connects to the signal processing module 106. The signal processing module 106 may be connected to an exterior portion of the frame 110. The data bus or conduit 118 may route to the outside of the frame 110, via an exit pathway, to connect with the signal processing module 106.

In FIG. 3D, the conduit opening 364 is formed as a rectangular opening on the second base surface 316 of the base frame 112. In this design, the rectangular opening is 3.0 mm×5.0 mm. The conduit opining 364 extends through a portion of the channel extrusion 346 on the base inner surface 310. The covering piece 114 also includes the conduit opening 364 and also a rectangular cut-out. The rectangular cut-out may extend from the second cover surface 326 to the channel 360. The rectangular cut-out in this design is 2.0 mm×5.0 mm.

While the various components and internal structures of the frame (e.g., channels 360 and cavities 362 for sensors 104a-104n and conduit 118 in the covering piece 114 and the corresponding extrusions 340 in the base frame 112) have been designed to hold each piece of the frame 110 securely, the flexible nature of the materials used for the base frame 112 and covering piece 114 could cause them to separate during use. To minimize or avoid this separation, the frame 110 employs specially designed screw sets 370 as an "interlocking mechanism" to hold the base frame 112 and covering piece 114 together. The screw set 370 includes screw pegs 372 having a length that can pass through the screw holes 374 formed in the base frame 112 and the covering piece 114 to be capped by screw caps 376. The interlocking mechanism can additionally provide a means to secure the breathable filter 120 to the respiratory protective device frame 110 during its use. The screw holes 374 can extend from the base inner surface 310 to the base outer surface 312 and from the cover inner surface 320 to the cover outer surface 322, respectively.

Screw-Set Location. In this design, the frame 110 includes three locations for the set screws 370: (i) at the top center (374a), (ii, iii) on either side of the frame 110 (376b). FIG. 3E shows example locations of the three interlocking positions and the locations of the screw holes 374, as shown in subpanel (D). In FIG. 3E, the top center screw hole 374a is formed by first determining a line between two base contours at the top center, coincident with the nose bridge apex 332, as shown in subpanel (A). Then, the midpoint "L1" 375 of that line would be the center point of the top center screw hole 374a. The side screw holes 374b are formed by dividing a first sensor location "S3" and a second sensor location "S5" into three segments: the one-third point from "S3" is marked "L2" 377 as the center point of the side screw hole 374b, as shown in subpanel (B). The other screw hole 374b can be determined at a mirrored position "L3" 377', as shown in subpanel (C).

FIG. 3F (top screw hole) shows example dimensions and configurations of the base outer surface 312 (in subpanel (B)), and base inner surface 310 (in subpanel (A)) for the region associated with top screw holes region 374a. In the base frame 112, the top center screw hole 374a, in this design, is defined by two holes that are 5 mm×2.5 mm with a corner fillet radius of 0.25 mm with a gap distance of 2 mm. In the covering piece 114 (shown in subpanels (C) and (D)), the top center screw hole 374a is also defined by two holes having the same dimensions as that of the base frame 112.

FIG. 3G (side screw hole) shows example dimensions and configurations of the base outer surface 312 for the region associated with the side screw holes 374b. In the base frame 112 (shown in subpanels (A) and (B)), the side screw hole 374b is also defined by two holes having the same dimensions as that of the top screw holes 374a. In the covering piece 114 (shown in subpanels (C) and (D)), the side screw hole 374b includes the two holes recessed in a rectangular base hole 378, in this design, having dimensions of 7.5 mm×5.5 mm with a depth of 1.25 mm.

FIGS. 3H-3K show views of the set screws 370 for the top and the side holes. Each set screw 370 includes a screw base 380, two screw pegs 372, and a dissected cylindrical screw 386 with helical threads 388. FIGS. 3H and 31 show the top center screw holes 374 and FIGS. 3J and 3K show the side screw holes 370b.

In FIGS. 3H and 31 (top screw), the screw 370a includes a screw base 380a that has a contoured base surface 382a matching that of the corresponding cover inner surface 320 in which it sits. Two screw pegs 372 are connected to an underside surface 384 of the screw base 380 in which the contoured base surface 382 is opposite and spaced apart from the underside surface 384. The two screw pegs 372 each extend away from and substantially perpendicular to the underside surface 384. The two screw pegs 372 include a section with helical threads 388 to mate with a screw cap 376. The dissection of the dissected cylindrical screw 386 forms the two rectangular screw pegs 372 to be extended through the screw holes 372 in the base frame 112 and the covering piece 114. The dissected cylindrical screw 386 is chamfered at the front edge.

The screw base 380, in this design, is 7.5 mm×5.5 mm (as shown in subpanel (B) or FIG. 31) to fit frictionally in the base hole 378 on the covering piece 114 with a gap of 2 mm. The two rectangular screw pegs 372 are each 4.75 mm×2.25 mm to fit smoothly through the two screw holes 372 and extends with a length of 11 mm (as shown in subpanel (C) or FIG. 31). The dissected cylindrical screw 386 has a diameter of 6 mm (as shown in subpanel (A) of FIG. 31) with a helical pitch of 1 mm in five turns; the helix pipe diameter is 0.5 mm.

FIGS. 3J and 3K (side screw) show an embodiment of the set screws 370 designed for the side screw holes 370b. The screw base 380b on the side of the frame 110 includes a flat surface matching that of the corresponding inner cover surface in which it sits. Most elements and example dimensions are the same as the top center set screw embodiment (as shown in subpanels (A) and (B) of FIG. 3K), except the screw base has a thickness of 1.25 mm (as shown in subpanel (C) of FIG. 3K).

FIGS. 3L and 3M (screw cap) show an embodiment of the screw cap 376 designed for coupling to the set screws 370. The screw cap 376 includes an inner cap surface 390 with helical threads 392 configured to mate with corresponding helical threads 388 in the set screw 370. The outer cap surface 394 is shaped as a truncated cone having a wide end 396 and a narrow end 398. The wide end 396 helps to hold the breathable filter 120 in place when the screw cap 376 engages with the set screws 370. The breathable filter 120 is secured between the frame 110 and the screw cap 376. More specific dimensions of the screw cap 376 are shown in subpanels (A), (B), and (C) of FIG. 3M.

FIGS. 3N, 30, 3P, and 3Q (frame hooks) illustrate fastening hooks 900 disposed on the base frame 112. Multiple fastening hooks 900 are shown placed along the second base surface 316 of the base frame 112 between the zygomatic and jaw side point (marked D2). A user can choose specific fastening hooks 900 to engage with fastening straps (not shown) to ensure the optimal fit of the respiratory protective device 102. In FIG. 3N, the dimensions of fastening hook 900 are shown with the hook configured as a hollow squared box shape with rounded edges. In this embodiment, the outer square edge is 10 mm with a corner radius of 1 mm, while the inner square edge is 6 mm with a corner radius of 1 mm. The thickness of each fastening hook 900 is 6 mm. In FIGS. 3P and 3Q, the fastening hooks 900 are shown as implemented on the frame. To place the hooks, as shown in FIG. 3Q, from the zygomatic (8), the midpoint "H1" (center of the first fastening hook 901) is identified for the second base surface 316. The fastening hooks 900, in this design, are placed 12 mm apart (center-to-center) and aligned along the second base surface 316. The fastening hooks 900 are repeated until the jaw side point "D2" region.

FIGS. 3R and 3S (frame reinforcement and covering piece assembly) show the cross-section of the base frame 112 having wing flaps 334 at the connection between the base frame 112 (as shown in subpanel (A) of FIG. 3R) and covering piece 114 (shown in FIG. 3S) to provide frame reinforcement at that section and to retain the covering piece 114. The wing flaps 334 include an extension that extends on both side of the base frame 112 from the edges 315, 317 of the first and second base surface 314, 316. The wing flaps 334, in this design, have an extending region of 3 mm and a thickness of 1 mm thickness adjacent to the edges 315, 317, as shown in subpanel (B) of FIG. 3R. The wing flaps 334 tapers to a wing flap end 336 to form a wedge shape. The result is a flexible wedge shape that can secure the covering piece 114 within the base frame 112 to form the complete frame 110, as shown in the cross section of FIG. 3S, subpanel (B).

Example Sensor-Integrated Respiratory Protective Device #2

FIG. 3T shows a second embodiment of the frame 111 configured as a unitary structure. In this configuration, the sensor network 103 and conduit 118 may be embedded into the frame 111 during manufacturing (e.g., by 3D printing and/or copper circuit board printing methods). The wiring may be formed using conventional wiring or with printed conductive paint.

Example Method of Fit Monitoring

Figure 4A:
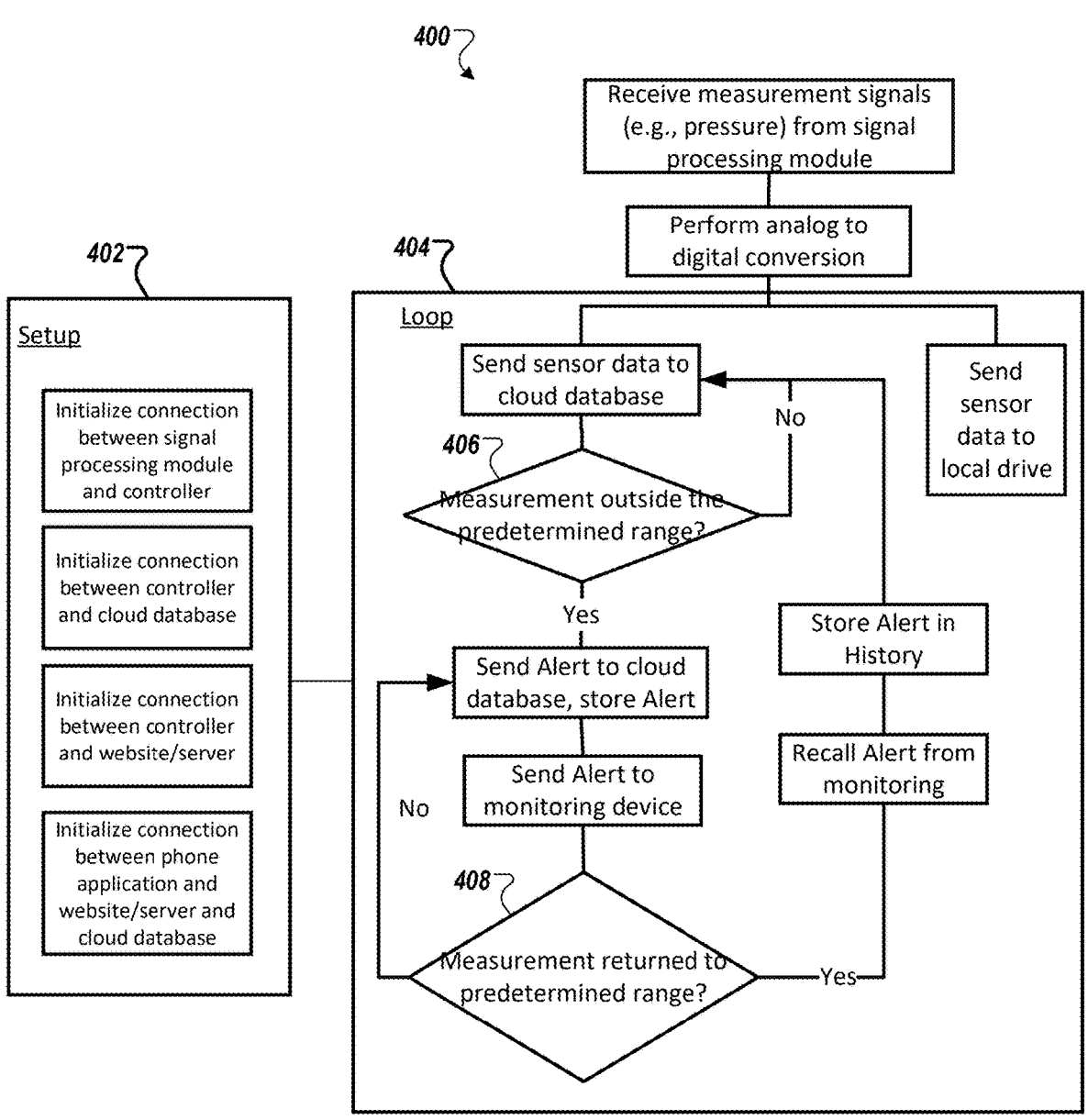
FIGS. 4A and 4B are flowcharts depicting example methods of operation to continuously monitor the fit of a respiratory protective device, according to one implementation.

FIG. 4A is a flowchart depicting an example method 400 to continuously monitor the fit of the respiratory protective device 102. Method 400 includes a setup sequence 402 for the system 100b to initialize connection between the signal processing module 106, the controller 108, the website/ server 136, and the cloud database 138. Method 400 includes the continuous fit monitoring loop 404.

In the example shown in FIG. 4A, the continuous fit monitoring loop 404 is performed on measured data received from the signal processing module. The measured data is stored to a local drive and transmitted to a cloud database 138.

The cloud database 138 performs a first pressure check step 406. If the pressure remains within predetermined values, the loop continues, and sensor data continues to relay as normal. If the pressure values fall outside of a predetermined range (e.g., too low indicating a leak, or too high indicating the danger of pressure injuries to a user), then the cloud database 138 sends an alert signal to the monitoring interface device 126 (e.g., a phone application 140), notifying a user. A second pressure check step 408 is performed to determine if the user has adjusted the respiratory protective device 102 to fix the pressure issue. If the pressure has not returned to the predetermined range, a second alert may be sent. If the pressure has returned to the predetermined range, the cloud database 138 recalls the alert, stores the alert in a history, and returns to normal sensor data gathering operation. In some implementations, the signal processing module 106 or controller 108 also relays signal data to a remote website/server 136 to enable remote monitoring of the respiratory protective device fit.

Figure 4B:
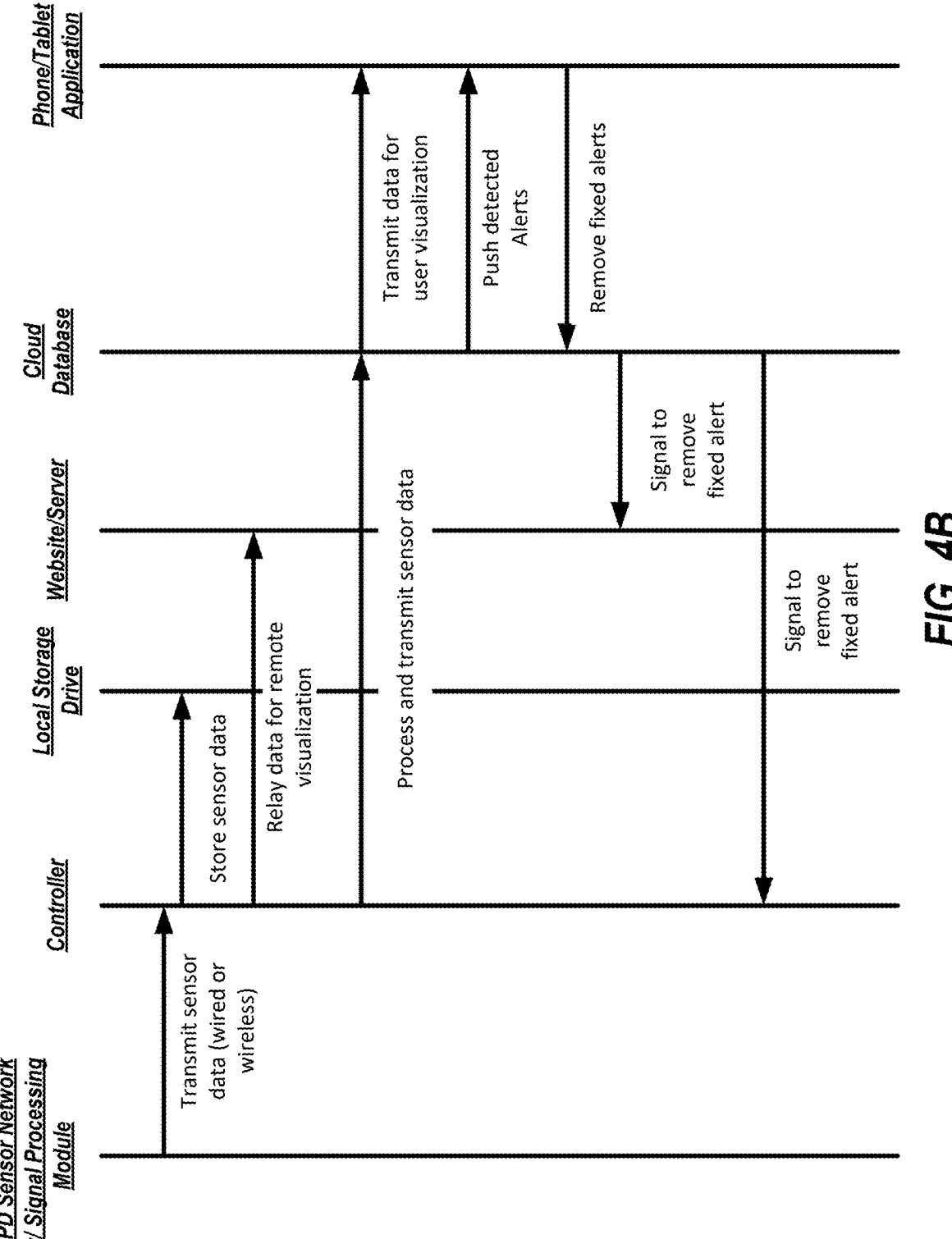

FIG. 4B is a flowchart depicting the back-end system of continuously monitoring the fit of the respiratory protective device 102. As shown, the respiratory protective device 102 with the signal processing module 106 transmits sensor data from the sensor network 103 to a controller 108. The controller 108 stores data in a local drive, relays data to a website/server 136 for remote visualization and transmits processed data to a cloud database 138. The cloud database 138 then interacts with the monitoring interface device 126 (e.g., a smart phone with a phone application 140), which can display data and/or alert a user.

Figure 5A:
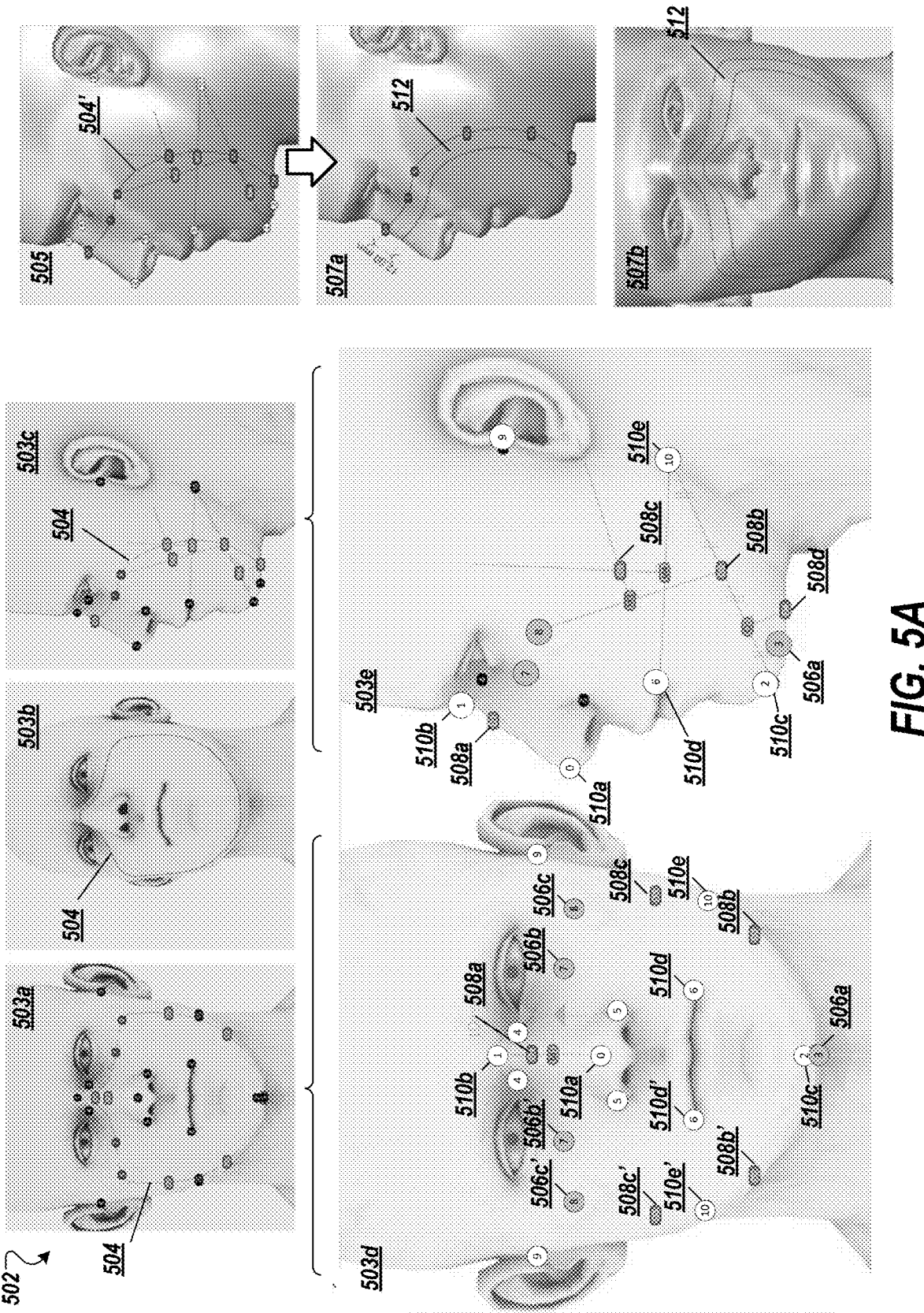
Figure 5B:
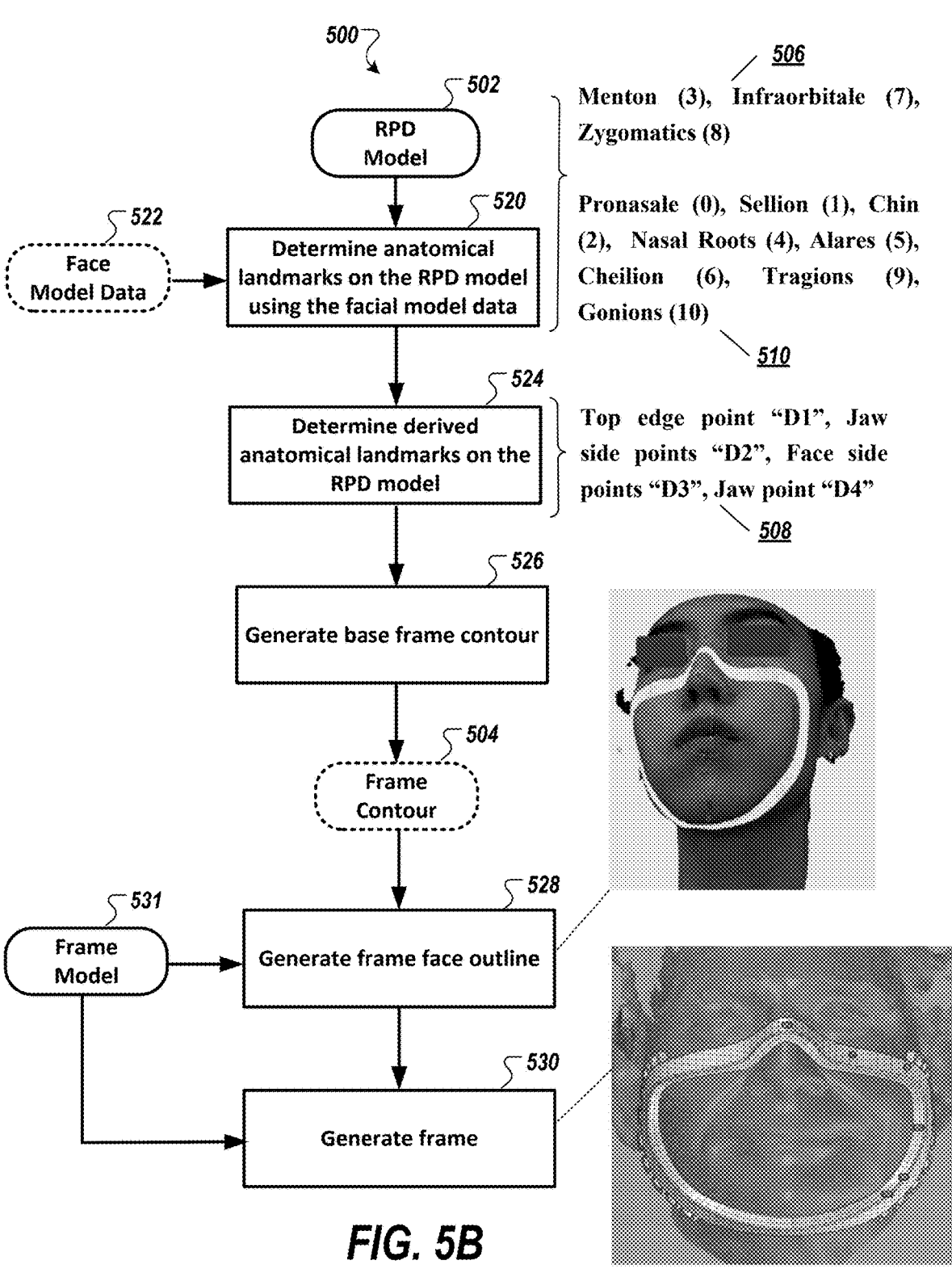
Figure 5D:
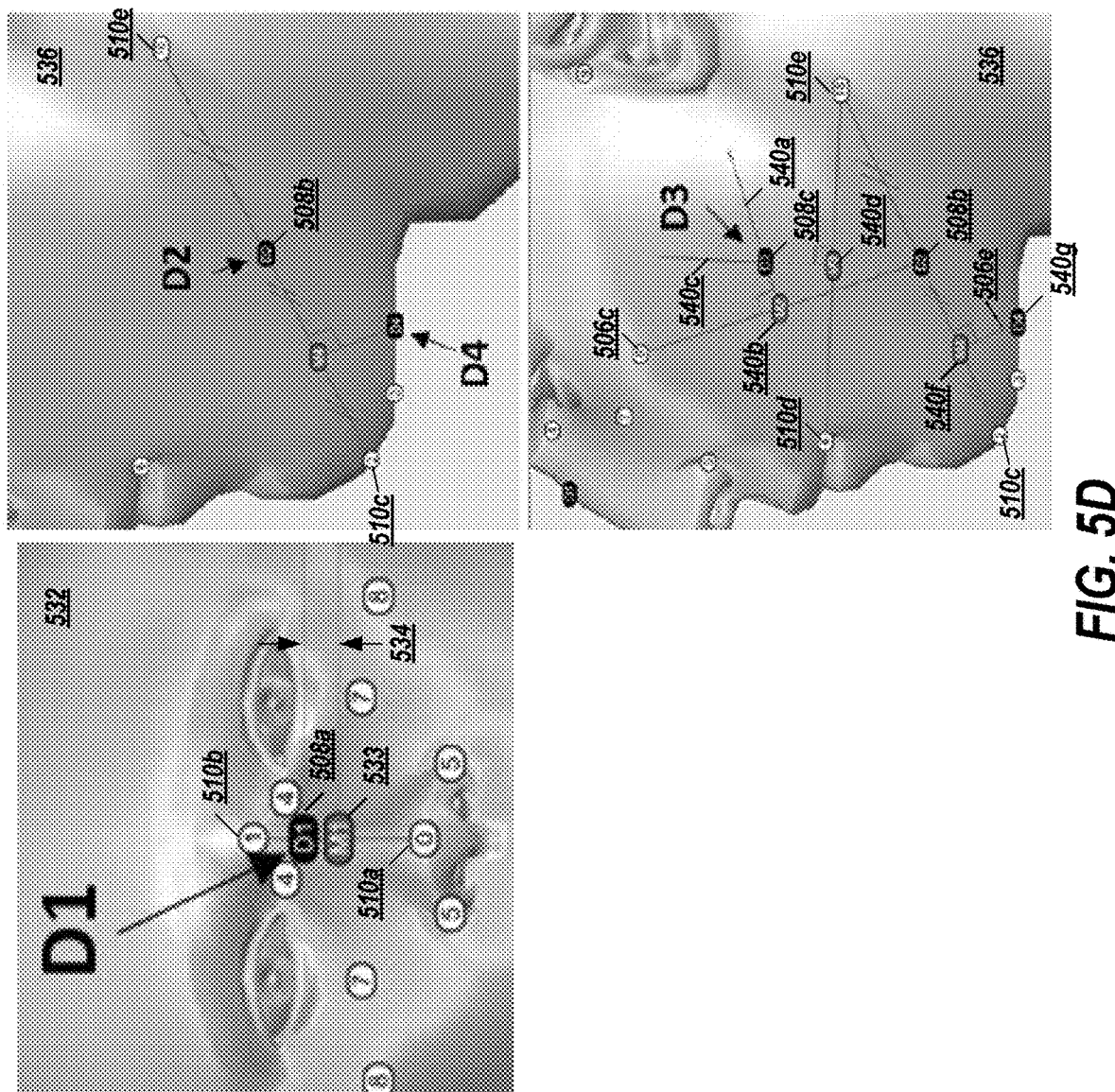

FIG. 5A shows landmarks within a respiratory protective device model 502 that defines a facial contour 504 (see diagrams 503a, 503b, 503c) for a respiratory protective device (e.g., 102). The facial contour 504 defines a base outline of the respiratory protective device and is defined by a set of anatomical landmarks 506 (shown as landmark "3" 506a, landmark "7" 506b and 506b', and landmark "8" 506c and 506c', see diagrams 503d, 503e) and landmarks 508 (shown as a derived landmark "D1" 508a, derived landmark "D2" 508b and 508b', derived landmark "D3" 508c and 508c', and derived landmark "D4" 508d, see diagrams 503d, 503e) derived from other anatomical landmarks 510 (shown as landmarks "0" (510a), "1" (510b), "2" (510c), "6" (510d and 510d'), "10" (510e)). The base outline of contour 504 (shown as 504' in diagram 505) can be expanded to generate the frame outline 512 (shown in diagram 507a and 507b). FIG. 5B shows an example method 500 to generate the facial contour 504 for the facial model 502. FIG. 5C shows example parameters for the dimensions of the landmarks in the respiratory protective device model 502.

Table 1 provides a list of the landmarks in the respiratory protective device model 502.

TABLE 1

| Contour Landmark | Anthropometrical and anatomical information usage | Description |
|---|---|---|
| Top edge point "D1" (508a) | Derived from Pronasale (point 0) and Sellion (point 1) | Determine from an offset of a midpoint "M1" between Pronasale (point 0) and Sellion (point 1) |
| Jaw side points "D2" (508b and 508b') | Derived from Chin (point 2) and Gonions (point 10) | Determine as a midpoint between Chin (point 2) and Gonions (point 10) |
| Face side points "D3" (508c and 508c') | Derived from Zygomatics Landmark "8," derived Landmark "D2," Cheilion (point 6), and Gonions (10) | Determine as an intersection of (i) a first line projecting from a midpoint "M2" between Zygomatics Landmark "8" and derived Landmark "D2" (ii) a second line projecting from a midpoint "M3" between Cheilion (point 6) and Gonions (10) |
| Jaw point "D4" (508e and 508e') | Derived from Chin (2) and Derived Landmark "D2" | Determine as a midpoint "M4" between Chin (point 2) and Derived Landmark "D2" |
| Menton Landmark "3" (506a) | Derived from Menton (3) | Determine as Menton (point 3) |
| Infraorbitale Landmark "7" (506b and 506b') | Derived from Infraorbitale (7) | Determine as Infraorbitale (point 7) |
| Zygomatics Landmark "8" (50cb and 508c') | Derived from Zygomatics (8) | Determine as Zygomatics (point 8) |

When an alert is pushed to a user, the system 100b checks to see if the user has fixed the issue. Once fixed, the phone application 140 removes the alert, and the cloud database 138 relays the fixed alert information to the website/server 136 and the controller 108.

Example Method of Respiratory Protective Device Customization

FIGS. 5A-5E illustrate an example method 500 to generate a customized respiratory protective device 102 from a model having a customized frame determined from pre-defined facial anthropometrical and anatomical landmarks that are adjusted for a specific user, e.g., based on the user's measured scan or measurement.

FIG. 5B shows an example method 500 to generate the facial contour 504 for the facial model 502.

Method 500 includes applying an RPD model 502 to face model data of a person. In instances in which the face model data is for a specific person, the resulting RPD is thus designed and customized for that person. In instances in which one or more general face models are employed, e.g., for different sizes and shapes, the RPDs are designed and customized to those models.

In operation 520, the face model data (e.g., a 3D model of a person's face, e.g., cloud, mesh, or geometric data) can be evaluated for a set of pre-defined landmarks, including the Menton (landmark "3" 506a), Infraorbitale (landmark "7" 506b), Zygomatics (landmark "8" 506c), Pronasale (land-mark "0" 510a), Sellion (landmark "1" 510b), Chin (landmark "2" 510c), Nasal Roots (landmark "4"), Alares (landmark "5"), Cheilion (landmark "6" 510d), Tragions (landmark "9"), and Gonions (landmark "10" 510e). The operation may be performed by the manual marking of a person's face with the above-noted landmarks, capturing an image or 3D scan of the facial, and importing a digital image or 3D scan into a 3D software. An example of a 3D scanner is the 3dMD system [14]. The scanner can capture a three-dimensional face image, e.g., ear to ear. The data may be stored as a point cloud, geometric mesh, triangular, or polygonal elements or framework. CAD software are available that can import scanned data and construct a 3D model. An example of the CAD software is Rhino CAD software.

The operation may also be alternatively performed using 3D face recognition technology. FIG. 5C shows example parameters for the dimensions of the landmarks in the respiratory protective device model 502.

Method 500 then includes determining (524) derived anatomical landmarks on the RPD model, e.g., the top edge point "D1" (508a), Jaw side points "D2" (508b, 508b'), Face side points "D3" (508c, 508c'), Jaw point "D4" (508d, 508d') as described in relation to FIG. 5A. In some embodiments, the method 500 may determine other derived landmarks for various landmarks described herein, e.g., 506b, 506c.

Top Edge Point Landmark "D1" (508a): To identify the location for the top edge point 508a of the frame, in the example shown in FIG. 5D, diagram 532, the system may employ the Pronasale (point "0" 510a, as the nose height) and Sellion (point "1" 510b) and determine the midpoint "M1" 533 between them (e.g., in the 3D model or with a 2D projection of the model). Based on existing FFR placement data, the average point of the top edge of the FFR is at 57% from the pronasale on the sellion-pronasale line. To accommodate the sensor network for continuous fit monitoring, the system may increment the midpoint "M1" 533 with a pre-defined length 534, e.g., 10 mm for the frame. In some embodiments, a line can be drawn in a projection view of the model, and the midpoint and above-noted offset point can be determined. The determined points in the projection can be projected to a 3D model of the face. In other embodiments, the line can be drawn in the 3D coordinate space of the 3D model of the face, and the midpoint and above-noted offset point can be determined in that 3D coordinate space.

Jaw side points "D2" (508b): To ensure that the frame fits well on the side of the face with no leakage, it is observed that the frame should have a smooth contour near the jaw and the sides of the face. In the example shown in FIG. 5D, diagram 536, the pair of jaw side points between the chin point "2" 510c and gonion "10" 510e is determined (e.g., in the 3D model or with a 2D projection of the model) as a midpoint between them. In some embodiments, a line can be drawn in a projection view of the model, and the midpoint can be determined. The determined points in the projection can be projected to a 3D model of the face. In other embodiments, the line can be drawn in the 3D coordinate space of the 3D model of the face, and the midpoint determined in that 3D coordinate space.

Face side points "D3" (508c): To ensure a proper fit and a smooth contour on the side of the face with a lot of soft tissue, it is observed that the frame should have one or more "intermediate" points among landmarks along the side of the side. In the example shown in FIG. 5D, diagram 538, the face side points "D3" 530c is determined (e.g., in the 3D model or with a 2D projection of the model) as an intersection of (i) a first line 540a perpendicularly projecting from a midpoint "M2" 540b defined between the Zygomatics Landmark point "8" 506c and derived Landmark "D2" 508b (ii) a second line 540c perpendicularly projecting from a midpoint "M3" 540d between Cheilion (point "6" 510d) and Gonions (point "10" 510e). In some embodiments, a line can be drawn in a projection view of the model, and the derived landmarks can be determined. The determined points in the projection can be projected to a 3D model of the face. In other embodiments, the line can be drawn in the 3D coordinate space of the 3D model of the face and the derived landmarks determined in that 3D coordinate space.

Jaw point Landmarks "D4" (508d): To ensure the contours of the frame fit well on the face near the Menton (point "3" 506a), in the example shown in FIG. 5D, diagram 536, the jaw point landmark "D4" 508d is determined (e.g., in the 3D model or with a 2D projection of the model) as an intersection of (i) a line 540e perpendicularly projecting from a midpoint "M4" 540f defined between Chin (point "2" 510c) and Derived Landmark "D2" and (ii) a contour 540g of the jaw. In some embodiments, a line can be drawn in a projection view of the model, and the derived landmarks can be determined. The determined points in the projection can be projected to a 3D model of the face. In other embodiments, the line can be drawn in the 3D coordinate space of the 3D model of the face and the derived landmarks determined in that 3D coordinate space.

Figure 5E:
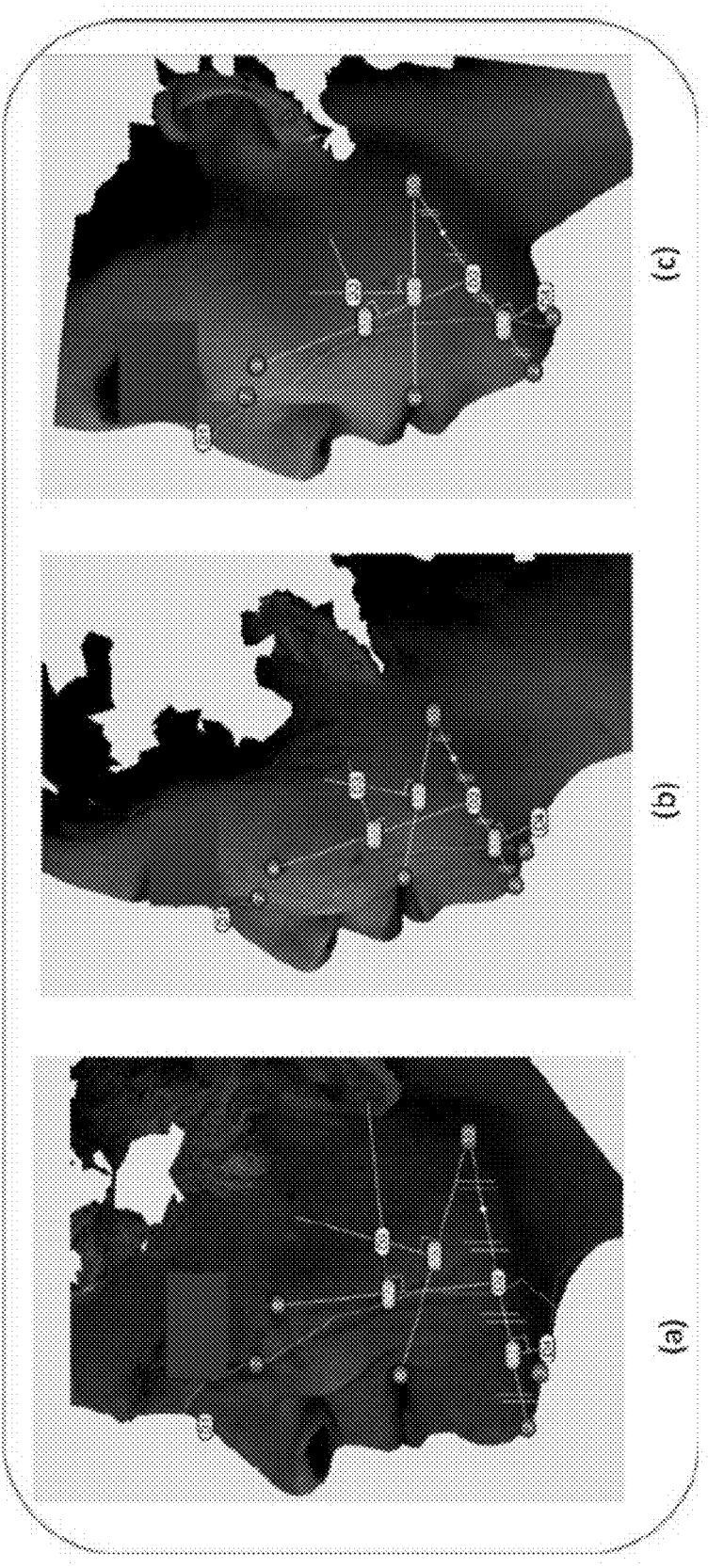

Method 500 then includes generating (526) a base frame contour 504. In some embodiments, the contour is generated by interpolating (e.g., via curvilinear interpolating or other smoothing interpolation) between the defined landmarks, e.g., 508a, 506b, 506c, 508c, 510e, 508b. 506a, 508b', 508c', 506c', 506b'. The operation may be performed (i) for the full face or (ii) for half of the face and mirrored for the other half. The contour is then projected on to the scan data with the face shape for each subject. FIG. 5E shows the base frame contour 504 for three different subjects.

In some embodiments, the operation begins with the top edge point (D1) in the side view; interpolation is then performed between the points infraorbitale (7), zygomatic (8), the face side point (D3), the jaw side point (D2), and the jaw point (D4). This is then projected onto the face scan to obtain the frame contour that wraps onto the facial profile.

Method 500 then includes generating (528) a frame face outline 512. In the example shown in FIG. 5A, an offset of 12 mm inwards is made to accommodate the sensor network. It has been determined that 12 mm is the optimum surface width of the respiratory protective device frame to rest well on the face of an adult. Then, a projection of both contours onto the facial profile scan is performed to create the 3D base frame contours. Other offsets may be used.

Method 500 then includes generating (530) the frame 102, further described below.

Taxonomy of Landmarks: A taxonomy is employed for the set of facial landmarks for developing the custom-fit respiratory protective device. As shown in FIG. 5C, the Defined Landmarks are those obtained in part from literature and which serve as the basis for identifying additional landmarks for developing the contour of the respiratory protective device frame. These Defined Landmarks are classified into Guiding Landmarks and Construction Landmarks. The Guiding Landmarks can guide the design of the customized frame; for example, pronasale (0) can serve as the origin (0, 0, 0) for the computations. The Construction Landmarks are used for constructing the final contour of the frame. The various intermediate landmarks that served to develop the final set of landmarks—based on geometrical relationships with the Defined Landmarks—are called Process Landmarks. These Process Landmarks are used to derive the Derived Landmarks. Thus, the customized frame contour is constructed using the Construction Landmarks and Derived Landmarks.

This taxonomy has a critical role to play in designing and developing a custom-fit respiratory protective device to fit any facial profile. The Derived Landmarks are based on well-defined steps (algorithms) drawing upon the Defined Landmarks as the foundation. Therefore, the process of creating a customized contour for any facial profile can be automated using the algorithms underlying the taxonomy shown in the figure. FIG. 5F shows the locations of the various facial landmarks in the taxonomy.

Customized Sensor Location and Frame Generation

Figures 6A, 6B, 6C, 6D:
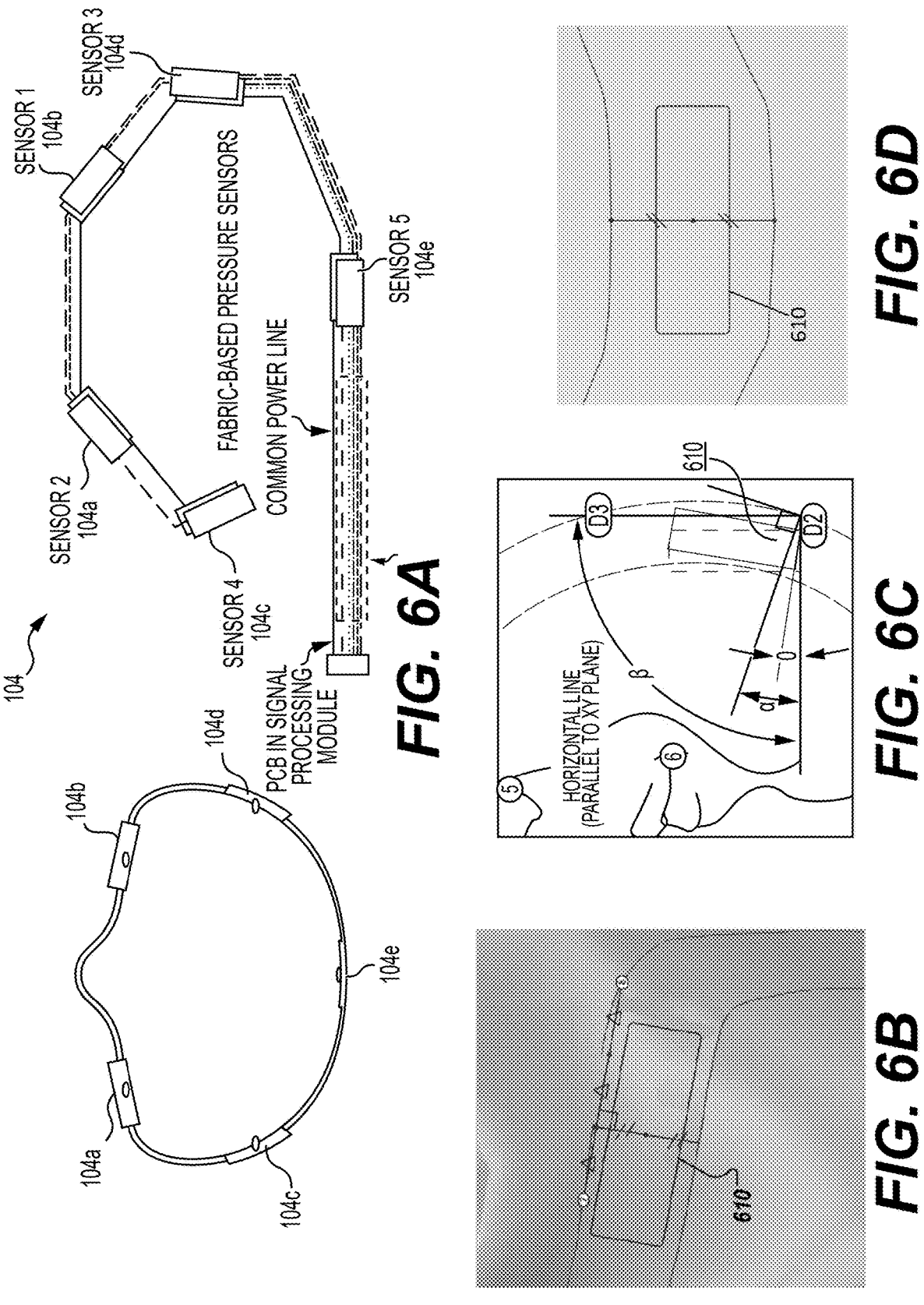
FIG. 6A shows a schematic of the fabric-based sensor network of the continuous fit monitoring system, according to one implementation.
FIGS. 6B-6D each illustrates a process of locating a sensor on a frame of a respiratory protective device or customizable device, according to one implementation.

FIGS. 6A-E illustrate an example method for generating the frame 110 of the respiratory protective device 102 with customized sensor 104a-104n location on the frame 110. A digital scanning system analyzed traditional Filtering face-piece respirators (FFR) usage and changes in facial profile during a variety of activities (e.g., talking, smiling, yawning). Faces were scanned using the 3dMD system. Analysis was performed to determine the locations to ensure the sensors stayed in place with changes in the facial profile. As shown in FIG. 6A, two sensors 104a, 104b— one on either side of the nose bridge—will be located around the infra-orbitale and zygomatic areas; third and fourth sensors 104c, 104d, each will be placed symmetrically on either side of the face, and the fifth sensor 104e will be centrally located at the bottom of the frame near the chin. Thus, the sensors 104a-104e at these five locations around the face seal will ensure continuous monitoring of the fit as the facial profile changes when the respiratory protective device 102 is in use.

FIG. 6A shows the schematic of the fabric-based sensor network 103 of the continuous fit monitoring system 100a,b. It consists of five sensors (20 mm×5 mm) distributed around the respiratory protective device frame 110. The signals from these sensors 104a-104e are carried by the conductive data buses 118 to the signal processing module 106 outside the frame. This sensor network 103 is integrated into the respiratory protective device frame 110 by creating the necessary slots and pathways to accommodate the sensors 104a-e and the data buses or conduit 118, respectively.

Algorithms for Placement of Sensor Slots in RPD Frame: FIGS. 6B-6E show the algorithms for locating the slots for sensors 104a-e (S1 through S5). The sensor cavity outline 610 for each sensor cavity 362 (not shown in FIG. 6B-E) will be a 25 mm×8 mm rectangle to accommodate the 20 mm×5 mm sensor 104a-104e.

The 2D mapping of the front face view may be used to determine the locations for the slots for sensors 104a, 104b (shown as "S1" and "S2") as shown in the algorithm in FIG. 6B. For the sensors 104a, 104b ("S1" and "S2"), the first step is to draw a line between the infraorbitale (7) and the zygomatic (8). From the infraorbitale, find the one-third point on the 7-8 line and drawn a line perpendicular to that point towards the inner and outer contours of the frame, as shown in FIG. 6B. The midpoint of that perpendicular line will be the center point of the sensor cavity outline 610 and of the slot of sensor 104a, S1. Steps can be mirrored for sensor 104b, S2.

The 2D mapping of the side face view may be used to determine the location of the slots for sensors 104c, 104d ("S3" and "S4"). As seen in the algorithm shown in FIG. 6C, the locations of the sensor cavity outline 610 are dependent on the facial profile, specifically the relative positions of the landmarks "D2" and "D3." Thus, the algorithm accommodates the range of facial profiles. To find the slots for sensors 104c, 104d ("S3" and "S4"), start from "D2" and construct a horizontal line in the X-Y plane until it intersects the inner frame contour. From the midpoint of that line segment between the two contours, construct a 25 mm×5 mm rectangle using the midpoint as the bottom edge center in the vertical direction, shown as a dotted line in FIG. 6C. Then, draw a straight line between "D2" and "D3." Then, construct a tangent at "D2" and draw a perpendicular line at "D2" on the inner contour. Measure the angle ($\alpha$) between the horizontal line and the perpendicular line at D2 and the angle ($\beta$) between the horizontal line at "D2" and the "D2-D3" line. Based on the values of a and $\beta$, compute the angle ($\theta$) by which the rectangular sensor slot should be rotated, as shown in FIG. 6C. For example: (i) if $\beta<90°$, $\theta=0$; (ii) if $\beta=90°$, $\theta=0.5\alpha$; (iii) if $\beta>90°$, $\theta=0.9\alpha$.

For the slot for sensor 104e (S5), on the front 2D mapping, the principal longitudinal axis is extended along the sagittal plane until it intersects with the frame contours in the perspective view. FIG. 6D shows the algorithm for locating the slot for sensor 104e ("S5"). At the bottom center of the frame, draw a vertical line connecting the two contours of the frame. Find the midpoint of that line, which will be the center point for the bottom sensor 104e ("S5"). Construct the sensor cavity outline 610 with the midpoint as the center of the rectangle.

Figure 6E:
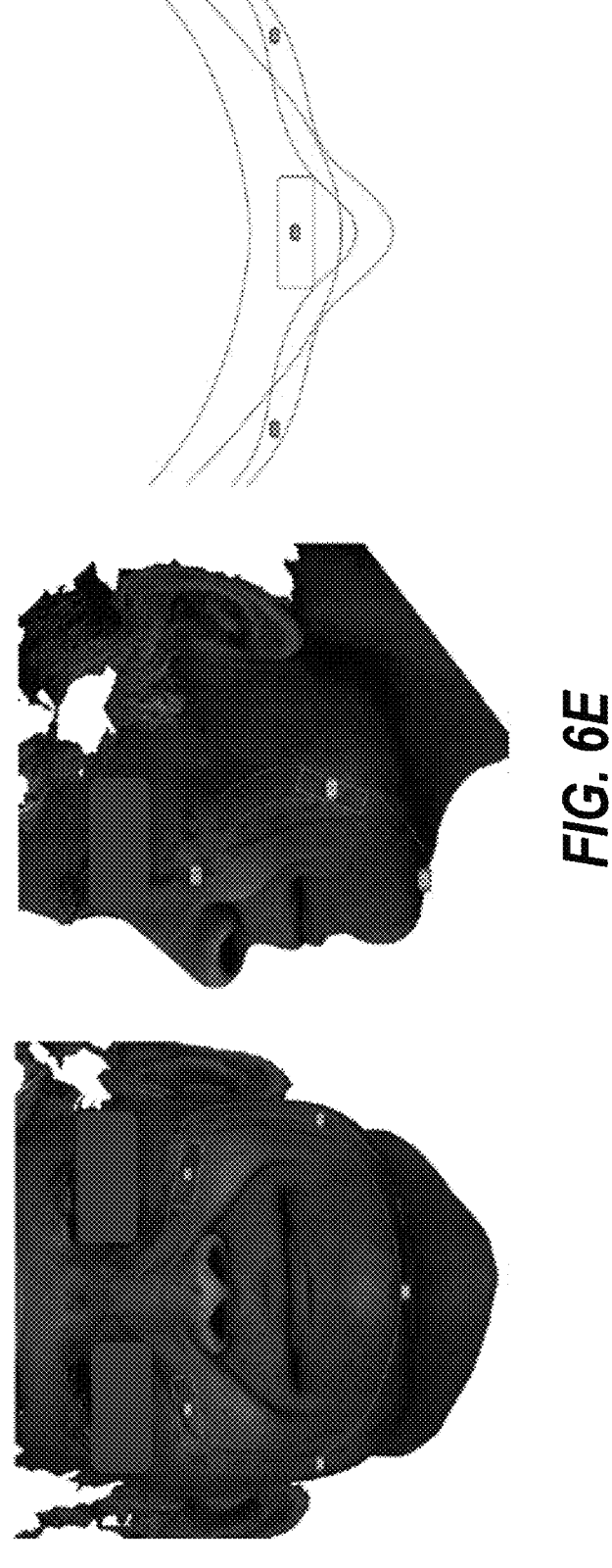
FIG. 6E depicts the contour of a frame generated using the process of FIGS. 6A-6D as located on a subject, according to one implementation.

Accommodating the Fit Monitoring Sensor Network: Placement algorithms from FIGS. 6B-6D were applied to incorporate the sensor slots into the frame 110. Rectangular slots were constructed with 25 mm length, 8 mm width, and 0.5 mm edge radius on the 2D mapping and then projected onto the frame base surface. As shown in FIG. 6E, for sensors 104a, 104b ("S1" and "S2"), the rectangular shapes were sketched on the 2D front view mapping. For sensor 104c, 104d ("S3" and "S4"), the rectangular shapes were sketched on the 2D side view mapping. For sensor 104e ("S5"), the rectangular slot was sketched from the top view.

Example Monitoring Application

FIG. 7A shows the user dashboard 700 in the App 140 running on an Android tablet along with the visualization of the pressure heat map 702. The menu options shown on the left in the dashboard include View Visualizations, View Pending Alerts, View History of Alerts, View Profile, and Logout. The View Visualizations option displays the color-coded pressure heat 702 maps to reflect the magnitude of the pressure under each sensor 104a-n. The color thresholds for the heat map 702 can be configured in the App to suit the requirements. In the figure, the ADC (analog to digital) values are displayed. When the option to display the pressure in psi is chosen in the App 140, the pressure will be displayed in lb/in2.

When the face seal pressure falls below a certain threshold under one of the sensors 104a-n, an alert is sent to the user's App 140 on the monitoring interface device 126 with a message to adjust/tighten the respiratory protective device 102. Those alerts are stored under "Pending Alerts" implying that the potential for a face seal leakage is high unless the user corrects the position of the respiratory protective device 102. When the user adjusts the respiratory protective device 102, the system 100a, 100b detects the change in pressure. If it meets the defined threshold, the alert is removed from Pending Alerts and stored in "History of Alerts." These alerts can be analyzed at a later date to understand the performance of respiratory protective device 102 over time and to spot any specific trends or activities during use that lead to face seal leakage. This type of data analytics, facilitated by the unobtrusive means to monitor pressure data in real-time, will be valuable in enhancing the design of respiratory protective devices (RPDs). The "User Profile" option in the menu is used to enter information about the user, which can then be correlated with other data to enhance the personalization of the device.

FIG. 7B shows an example sequence of operations during the typical use of the custom-fit respiratory protective device with integrated continuous fit monitoring.

When the user chooses the "View Visualizations" option in the main menu, the pressure heat map 702 is displayed as shown in FIG. 7B(panel a). Since the top-left and left sensors 104a, 104b, are below the threshold value set in the App 140, it generates two alerts to the user indicating areas of potential face seal leakage. When the "View Pending Alerts" option is chosen, the two alerts 704 are displayed as in FIG. 7B(panel b). FIG. 7B(c) shows alert 704 to the user. The alert may include suggestions (static text or dynamically generated output based on the sensor reading) to adjust the respiratory protective device 102. When the user adjusts the respiratory protective device 102, the pressure in the top left sensor 104a goes above the set threshold, as shown in FIG. 7B(panel d), and that alert 704 is moved to "History of Alerts." However, the user has not adjusted the respiratory protective device 102 in the area under the left sensor 104b; therefore, the alert 704 for the left sensor 104b remains as shown in Pending Alerts in FIG. 7B(panel e).

All the pressure values, alerts, and actions are stored in the database and can be retrieved for carrying out data analytics to understand the performance of the respiratory protective device over time. The data can also be used to identify the potential for a pressure injury from donning the respiratory protective device for long periods of time and alerting the user to prevent a pressure injury. In short, the developed custom-fit respiratory protective device with the integrated continuous fit monitoring system can become an unobtrusive data acquisition platform for research and development of respiratory protective devices, including human factors associated with the use of respiratory protective devices both in real-time and over time in workplaces with inhalation hazards.

Once the App was tested successfully, a series of tests were performed to evaluate the responsiveness of the respiratory protective device to changes in facial profile and calibration phase of the respiratory protective device. The positions of the straps can be marked to facilitate quick and correct donning during repetitive use. Subsequently, any changes from the baseline (within a defined threshold) during use will be detected by the App resulting in an alert to the user to adjust the frame to prevent leakage and ensure protection against the inhalation hazard.

FIG. 7C shows the ADC values displayed in the App 140, which correspond to the pressures in the five sensors 104a-e prior to donning by the subject. Since the pressure at the face seal measured in psi will be low, we use ADC values to demonstrate the responsiveness of the sensor network to small changes in pressure with facial movement.

The effect of changes in facial profile was tested—from natural to talking to smiling and to yawning—on the pressure distribution in the face seal on Subject A. In the subject's natural state, the pressure in the chin sensor is greater when compared to data prior to donning. In the talking state, the pressure is higher in all the sensors. In the smiling state, there is a change in the pressure values from the talking state, albeit by a small amount. In the yawning state, the pressure has increased significantly in the chin sensor.

Thus, this series of tests demonstrates the responsiveness of the custom-fit respiratory protective device to changes in facial profile and the quantification of the changes in pressure at the face seal by the continuous fit monitoring system through the App running on an Android tablet.

Testing and Evaluation of Example Embodiment

A series of benchtop tests were conducted to characterize the performance of the sensor network in the continuous fit monitoring system. The load on the individual sensors was increased from zero to 500 grams. The system recorded the corresponding ADC value. As seen in the change in ADC values in Table 2, showing the measured sensitivity for analysis of the sensors, the sensor network is responsive to small changes in the applied load. These results demonstrate the sensitivity and resolution of the sensor network, which are important for detecting even minor changes in pressure at the face seal during respiratory protective device use.

TABLE 2

| Load (gm) | Load (lb) | Pressure (lb/in^2) | ADC Value Sensor 1 (Top Left) | ADC Value Sensor 2 (Top Right) | ADC Value Sensor 3 (Left) | ADC Value Sensor 4 (Right) | ADC Value Sensor 5 (Bottom) |
|---|---|---|---|---|---|---|---|
| 0 | 0.00 | 0.00 | 19 | 19 | 19 | 19 | 40 |
| 5 | 0.01 | 0.07 | 29 | 29 | 24 | 21 | 61 |
| 10 | 0.02 | 0.14 | 68 | 62 | 37 | 51 | 73 |
| 20 | 0.04 | 0.28 | 78 | 86 | 41 | 75 | 124 |
| 50 | 0.11 | 0.71 | 170 | 190 | 100 | 149 | 208 |
| 100 | 0.22 | 1.42 | 225 | 267 | 180 | 215 | 280 |
| 200 | 0.44 | 2.85 | 390 | 428 | 269 | 309 | 380 |
| 500 | 1.10 | 7.11 | 452 | 484 | 336 | 403 | 438 |

Sensor Size: 20 mm × 5 mm quantification of the resulting changes in the pressure at the face seal. These tests were carried out on a subject. The respiratory protective device was connected to the Fastening Hub using a set of straps. As the straps were tightened and loosened, the pressure at the face seal changed. These changes were reflected in the pressure values sensed by the network and displayed in the heat map in the App, thus demonstrating the responsiveness of the sensor network and the successful operation of the App. In practice, the "optimum" or baseline pressure at the face seal to ensure proper fit can be established during the very first donning or the Thus, the design methodology, including the development of algorithms to define a "standard" method for customization, has led to digital prototypes of all the components of the respiratory protective device customized to the facial profiles of individuals. The design and successful testing of the fabric-based sensor network have demonstrated the realization of another key technology building block of the custom-fit respiratory protective device with continuous fit monitoring.

21

Material Evaluation and Selection

The material used to create the respiratory protective device frame must effectively balance device fit with comfort. It must be shape-conformable and ensure the frame's structural integrity over repeated use and decontamination. In addition, the materials must be 3D-printable. A standard Ashby plot shows the relationship between density and Young's modulus of various classes of materials [15]. It also shows the relationship between Young's modulus and tensile strength [16].

Elastomer is the class of materials with the right combination of strength and flexibility that comes close to having the feel, softness, and flexibility of human skin. These characteristics can be important for the respiratory protective device since its usage over long durations should not cause pressure injuries. The materials in this class include ethyl-vinyl acetate, silicones, polyurethanes, and neoprene, among others. Furthermore, silicones fall into the class of flexible polymer foams, potentially making them ideal candidates for the respiratory protective device frame material.

Hardness is another important material property that should be considered in balancing comfort with the fit and hence protection. The Shore Hardness continuum for the various classes of materials was used to select materials [17]. The chosen material should be in the range of extra-soft and soft materials with a maximum Shore hardness of 00-60, but preferably up to 00-40.

Table 3 shows the example properties of silicone-based materials: Elastic 50A [18], SIL30 [19], SILASTIC 3D 3335 LSR [20], and AMSil [21].

the annual fit-testing, and reusability. To address these challenges, the concept of scanning an individual's face and creating a customized respirator frame into which a replaceable filter of desired protection level (e.g., N95) could be integrated was developed and led to a US patent [4].

Importance of Fit and Continuous Fit Monitoring in Respiratory Protection. The pressure exerted by the respirator on the face at the interface affects both the comfort of the wearer and the leakage at the interface, the face seal. Roberge et al. studied the importance of tethering devices that hold the respirator on the face on repeated doffing and donning [5]. They found "a progressive decline in the loads generated by the top and bottom tethering devices of the three models of N95 FFR tested over the course of multiple simulated donning, doffing, and wear periods in a 2.5-hr span." This change in load (and hence, pressure) on the face seal could alter the "fit" of the respirator leading to leakages and thereby compromising the degree of rated protection from the device. Zhuang et al. (2017) tested 101 different FFRs using 25 subjects [6]. Only 32% of the devices achieved acceptable fit in at least one of three donning for greater than 75% of participants [6]. Studies have shown that the pressure exerted by the tethering devices is inversely proportional to the contact surface areas of the face seal [7].

The pressure exerted by the respirator on the face seal influences the comfort and tolerability of the user. However, there is no "quantitative" metric or indicator upon which the user can depend to know that the device has been donned correctly and that they will be protected while being comfortable. That "sense of security" for healthcare profession-

TABLE 3

| Company | Material | Tensile Strength (MPa) | Tear Strength (kN/m) | Elongation @ Break (%) | Shore Hardness (A Class) | Material Type |
|---|---|---|---|---|---|---|
| Formlabs | Elastic 50A | 3.23 | 19.1 | 160 | 50 | Silicone Urethane Elastomer |
| Carbon 3D | SIL 30 | 3.5 | 10 | 350 | 30 | Silicone Urethane Elastomer |
| DOW | SILASTIC 3D 3335LSR | 8.3 | 0.05 | 5.25 | 50 | Liquid Silicone Rubber |
| Elkem | AMSil | 2 | 10 | 200 | 70 | Engineering Silicone |

In evaluating the materials, Shore hardness is the most important property because the respiratory protective device must be soft on the user's face. After a comparative analysis of the properties, it was decided that Elastic 50A and SIL 30 were potential candidates for creating the physical prototypes because their Shore A hardness was in the 30-50 range. Even though the Shore A hardness of Silastic from Dow was 50, its tear strength was only 0.05 kN/m, which was very low compared to the other two materials. Both SIL 30 and Elastic 50A are also compatible with cleaning solvents used for decontamination, including, but not limited to, bleach (NaClO, 5%), Sanitizer (NH4Cl, 10%), and ultraviolet radiation.

Discussion

The protection of healthcare workers in the event of an influenza pandemic is a national imperative, and personal protective equipment (PPE) is at the frontline of defense. The COVID-19 Pandemic has reinforced the importance of personal protective equipment, especially reusable respirators, for healthcare workers on the frontlines [1, 2, 3].

The three key challenges associated with using N95 respirators are the need to "fit" the respirator to the wearer, als using respirators in the field is a critical factor in enabling them to perform at their best under trying circumstances (e.g., during COVID-19) without being afraid of compromising their personal safety. Furthermore, continuous monitoring of respirator fit is critical for ensuring both the comfort and efficacy of the respirator during use. The ability to "calibrate" the fit (balancing leakage and comfort) with the measured pressure at the face seal will lead to increased compliance with the use of the respirator by healthcare professionals, thus enhancing their protection.

Prevention of Pressure Injuries from Respirators. Continuous monitoring of face seal pressure, a measure of fit, is critical for yet another reason, viz., preventing pressure injuries (ulcers) associated with the long-term use of respirators [8]. A tight-fitting respirator used continuously over long durations appears to cause skin irritation, injury, and pain [9, 10]. In fact, the cost of treating pressure injuries is estimated to be 2.5 times the cost of preventing them [11]. Therefore, fit monitoring data can facilitate "evidence-based" decision-making on the safe use of respirators. Cai et al., (2018) developed a force sensor system that was inserted between the FFR and the headform to measure the pressure at the face seal [12]. However, due to the limitations of the force sensor system, they could measure the contact pressure at only a single point at a time. Consequently, they could not concurrently monitor the fit throughout the face seal in real-time, which is critical to ensure the desired degree of protection to the user at all times [12].

In short, there is a critical need to design and develop a respiratory protective device that is customized to a user's facial features and can continuously monitor the fit. During the initial fit-test with such a device, the numeric baseline parameters will be established. If there are no changes to these values during use (even during a shift) or over time, there will be no need for the mandatory annual fit test. Any change in these values will trigger appropriate alerts leading to necessary interventions to remedy the fit.

Example Computing System

It should be appreciated that the logical operations described above of the monitoring application and in the appendix can be implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as state operations, acts, or modules. These operations, acts, and/or modules can be implemented in software, in firmware, in special purpose digital logic, in hardware, and any combination thereof. It should also be appreciated that more or fewer operations can be performed than shown in the figures and described herein. These operations can also be performed in a different order than those described herein.

The computer system is capable of executing the software components described herein for the exemplary method or systems. In an embodiment, the computing device may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device to provide the functionality of a number of servers that are not directly bound to the number of computers in the computing device. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or can be hired on an as-needed basis from a third-party provider. Some cloud computing environments may comprise cloud computing resources owned and operated by the enterprise as well as cloud computing resources hired and/or leased from a third-party provider.

In its most basic configuration, a computing device includes at least one processing unit and system memory. Depending on the exact configuration and type of computing device, system memory may be volatile (such as random-access memory (RAM)), non-volatile (such as read-only memory (ROM), flash memory, etc.), or some combination of the two.

The processing unit may be a standard programmable processor that performs arithmetic and logic operations necessary for the operation of the computing device. While only one processing unit is shown, multiple processors may be present. As used herein, processing unit and processor refers to a physical hardware device that executes encoded instructions for performing functions on inputs and creating outputs, including, for example, but not limited to, micro-processors (MCUs), microcontrollers, graphical processing units (GPUs), and application specific circuits (ASICs). Thus, while instructions may be discussed as executed by a processor, the instructions may be executed simultaneously, serially, or otherwise executed by one or multiple processors. The computing device may also include a bus or other communication mechanism for communicating information among various components of the computing device.

Computing devices may have additional features/functionality. For example, the computing device may include additional storage such as removable storage and non-removable storage including, but not limited to, magnetic or optical disks or tapes. Computing devices may also contain network connection(s) that allow the device to communicate with other devices, such as over the communication pathways described herein. The network connection(s) may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing devices may also have input devices (s) such as keyboards, keypads, switches, dials, mice, track-balls, touch screens, voice recognizers, card readers, paper tape readers, or other well-known input devices. Output device(s) such as printers, video monitors, liquid crystal displays (LCDs), touch screen displays, displays, speakers, etc., may also be included. The additional devices may be connected to the bus in order to facilitate the communication of data among the components of the computing device. All these devices are well known in the art and need not be discussed at length here.

The processing unit may be configured to execute program code encoded in tangible, computer-readable media. Tangible, computer-readable media refers to any media that is capable of providing data that causes the computing device (i.e., a machine) to operate in a particular fashion. Various computer-readable media may be utilized to provide instructions to the processing unit for execution. Example tangible, computer-readable media may include but is not limited to volatile media, non-volatile media, removable media, and non-removable media implemented in any method or technology for storage of information such as computer-readable instructions, data structures, program modules, or other data. System memory, removable storage, and non-removable storage are all examples of tangible computer storage media. Example tangible, computer-readable recording media include, but are not limited to, an integrated circuit (e.g., field-programmable gate array or application-specific I.C.), a hard disk, an optical disk, a magneto-optical disk, a floppy disk, a magnetic tape, a holographic storage medium, a solid-state device, RAM, ROM, electrically erasable program read-only memory. (EEPROM), flash memory or other memory technology, CD-ROM, digital versatile disks (DVD) or other optical storage, magnetic cassettes, magnetic tape, magnetic disk storage or other magnetic storage devices.

In light of the above, it should be appreciated that many types of physical transformations take place in the computer architecture in order to store and execute the software components presented herein. It also should be appreciated that the computer architecture may include other types of computing devices, including hand-held computers, embedded computer systems, personal digital assistants, and other types of computing devices known to those skilled in the art.

In an example implementation, the processing unit may execute program code stored in the system memory. For example, the bus may carry data to the system memory, from which the processing unit receives and executes instructions. The data received by the system memory may optionally be stored on the removable storage or the non-removable storage before or after execution by the processing unit.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language, and it may be combined with hardware implementations.

CONCLUSION

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or another organism, living or dead, or other biological or molecular structure or chemical environment, and may relate to particular components of the subject, for instance, specific tissues or fluids of a subject (e.g., human tissue in a particular area of the body of a living subject), which may be in a particular location of the subject, referred to herein as an "area of interest" or a "region of interest."

It should be appreciated that, as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to humans (e.g., rat, dog, pig, monkey), etc. It should be appreciated that the subject may be any applicable human patient, for example.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

All references cited and discussed in this specification are incorporated herein by reference in their entireties and to the same extent as if each reference was individually incorporated by reference.

REFERENCES

[1] Institute of Medicine. 2008. Preparing for an Influenza Pandemic: Personal Protective Equipment for Healthcare Workers. Washington, DC, https://doi.org/10.17226/11980.
[2] Institute of Medicine. 2006. Reusability of Facemasks During an Influenza Pandemic: Facing the Flu. Washington, DC, https://doi.org/10.17226/11637.
[3] National Academies of Sciences, Engineering, and Medicine. 2019. Reusable Elastomeric Respirators in Health Care: Considerations for Routine and Surge Use. Washington, DC: The National Academies Press. https://doi.org/10.17226/25275.
[4] Jayaraman, S., and Park, S., Respiratory Protection Device, U.S. Pat. No. 10,646,731, May 2020.
[5] Roberge, R., Niezgoda, G., Benson, S., Analysis of Forces Generated by N95 Filtering Facepiece Respirator Tethering Devices: A Pilot Study, Journal of Occupational and Environmental Hygiene, 9 (8), 2012, pp. 527-533.
[6] Zhuang, Z., Bergman, M., Lei, Z., Niezgoda, G. & Shaffer, R. (2017) Recommended test methods and pass/fail criteria for a respirator fit capability test of half-mask air-purifying respirators. J. Occup. Environ. Hyg. 14, 473-481. https://doi.org/10.1080/15459624.2017.1296233.
[7] Yang J, Dai J, Zhuang Z. Simulating the interaction between a respirator and a headform using LS-DYNA. Computer-Aided Design Appl. 2009; 6(4):539-551.
[8] Protecting facial skin under N95 face masks, National Pressure Injury Advisory Panel, https://cdn.ymaws.com/npiap.com/resource/resmgr/position_statements/NPIAP_-Mask_Injury_Infograp.pdf, Last Accessed: Jun. 19, 2020.
[9] Stokowski, L. A. (2020) A Step-by-Step Guide to Preventing PPE-Related Skin Damage. MedScape. Retrieved from https://www.medscape.com/viewarticle/929590.
[10] Lam, U-Nee., Siddik, Nur., Yussof, Shah., and Ibrahim, S. (2020) N95 respirator associated pressure ulcer amongst COVID-19 health care workers, Int Wound J. October; 17(5): 1525-1527, doi: 10.1111/iwj.13398.
[11] Oot-Giromini B, Bidwell F C, Heller N B, et al. Pressure ulcer prevention versus treatment, comparative product cost study. Decubitus 1989; 2(3):52-4.
[12] Cai, M., Li., H., Shen, S., Wang, Y, and Yang, Q. (2018) "Customized design and 3D printing of face seal for an N95 filtering facepiece respirator", Journal of Occupational and Environmental Hygiene, 15:3, 226-234, https://doi.org/10.1080/15459624.2017.1411598
[13] Zhuang, Z., & Bradtmiller, B. (2005) A Head-and-Face Anthropometric Survey of U.S. Respirator Users. J Occup Environ Hyg. November; 2 (11):567-76. DOI: https://10.1080/15459620500324727. PMID: 16223715.
[14] 3dMD. (2020) Retrieved from https://3dmd.com/products/.
[15] Granta. (2020) Chart from CES EduPack, ANSYS Granta. 2019.
[16] Ashby. (2008) The CES EduPack Database of Natural and Man-Made Materials, Version 1.0, Granta Design, Cambridge, UK, January 2008.

28

[17] Shore. (2020) "Shore hardness scale," https://www.smooth-on.com/page/durometer-shore-hardness-scale/, Last Accessed: Nov. 14, 2020.
[18] Formlabs. (2022a) Elastic 50A, https://formlabs.com/materials/flexible-elastic/. Last Accessed: Jun. 19, 2022.
[19] Carbon 3D. (2022) SIL 30, https://www.carbon3d.com/materials/sil-30, Last Accessed: Jun. 18, 2022.
[20] Dow. (2022) SILASTIC™ 3D 3335 Liquid Silicone Rubber, https://www.dow.com/en-us/pdp.silastic-3-d-3335-liquid-silicone-rubber-lsr.4137603z.html?productCatalogFlag=1#overview, Last Accessed: Jun. 18, 2022
[21] Elkem. (2019) Silicones 3D Flyer Industrial, https://www.elkem.com/silicones/brands/amsil/, Last Accessed: Jun. 18, 2022

What is claimed includes:

1. A system comprising:
a respiratory protective device comprising a frame having a contour that maintains a breathable filter covering over a facial region of a user, wherein the frame includes at least one sensor cavity, including a first sensor cavity; and
a sensor network coupled to the respiratory protective device, the sensor network comprising:
at least one sensor, including a first sensor, wherein the first sensor is disposed within the first sensor cavity to detect pressure or proximity at an interface between the frame and the facial region; and
a signal processing module in operative communication with the at least one sensor, the signal processing module configured to continuously detect the pressure or proximity at the interface between the frame and the facial region via the at least one sensor for continuously monitoring fit or particulate-filtering operation of the respiratory protective device.

2. The system of claim 1, wherein the signal processing module includes:
a communication interface configured to wirelessly communicate with a controller, wherein the controller is configured to (i) receive the pressure values, (ii) generate a notification based on the pressure values, and (iii) relay the notification to activate one of a display on a user interface, an audio device, or a haptic device.

3. The system of claim 1, wherein the at least one sensor cavity includes a second sensor cavity, wherein the at least one sensor includes a second sensor, and wherein the second sensor is disposed within the second sensor cavity to detect pressure or proximity of the frame at the second sensor cavity to the facial region.

4. The system of claim 1, wherein the at least one sensor is placed at a derived point on a user's facial anatomy, wherein the frame has the contour and the first sensor cavity over, or in proximity to, at least one of:
an infraorbitale facial region, a zygomatic facial region, or a region therebetween;
a chin point facial region, a gonion facial region, or a region therebetween; or
a menton facial region, a sagittal plane, or a region therebetween.

5. The system of claim 1, wherein the first sensor is configured to detect pressure between the user's facial region and the frame.

6. The system of claim 1, wherein the first sensor is configured to detect temperature or liquid.

7. The system of claim 1, wherein the breathable filter covering comprises a replaceable filter with a pre-defined filtration configuration.

8. The system of claim 1, wherein the system further comprises a fastening hub comprising fastening hooks and attachable straps.

9. The system of claim 1, wherein the frame comprises a first frame portion and a second frame portion, the first frame portion being couplable to the second frame portion to form the contour that maintains the breathable filter covering over the facial region and the first sensor cavity in proximity to the facial region.

10. The system of claim 1, wherein the frame is a unitary body.

11. The system of claim 9, further comprising:

a set of interlocking screws, including a first screw and a second screw, wherein the first screw is configured to be attached to a screw recess located in the frame to couple the first frame portion to the second frame portion and maintain the breathable filter covering in the contour of the frame.

12. The system of claim 1, wherein the at least one sensor is at least one of (i) a fabric-based sensor or (ii) a conductive material printed on a substrate comprising a textile fabric, a polyimide (PI) film, a polyethylene terephthalate (PET) film, or a polyacrylic acid (PAA) film.

13. The system of claim 1, wherein the at least one sensor is coupled to the signal processing module over a conductive material comprising fiber, yarn, film, or wire.

14. The system of claim 2, wherein the controller comprises a speaker, a light source, or a piezoelectric transducer.

15. The system of claim 3, wherein the first sensor is located at a chin position, the second sensor and a third sensor are located on a mid-cheek position, and a fourth and a fifth sensor are located on an upper-cheek position, or a combination thereof.

16. The system of claim 2, wherein the controller is configured to output pressure values of the at least one sensor to a monitoring application.

17. A method of monitoring fit of a respiratory protective device, the method comprising:

providing a respiratory protective device comprising:

a frame having a contour that maintains a breathable filter covering over a facial region of a user, wherein the frame includes at least one sensor cavity, including a first sensor cavity; and a sensor network coupled to the respiratory protective device, the sensor network comprising (i) at least one sensor, including a first sensor, wherein the first sensor is disposed within the first sensor cavity to detect pressure or proximity at an interface between the frame and the facial region; and (ii) a signal processing module in operative communication with the at least one sensor, the signal processing module configured to continuously detect the pressure or proximity at the interface between the frame and the facial region via the at least one sensor for continuously monitoring fit or particulate-filtering operation of the respiratory protective device;

continuously monitoring signal or derived values produced by the first sensor; and providing the signal or derived value to a controller for display or alert generation.

18. The method of claim 17, wherein the respiratory protective device is fabricated by:

3D printing the frame for the respiratory protective device;

placing/installing the first sensor in the first sensor cavity; and connecting the first sensor to the signal processing module.

19. The method of claim 18, further comprising:

producing an alert signal when at least one signal or derived value is outside of a predetermined range; and producing a removal signal to remove the alert signal when the at least one signal or derived value returns to the predetermined range.

20. A system comprising:

computing devices configured to operate with a respiratory protective device, wherein the computing devices are configured to continuously monitor fit of the respiratory protective device on a user, wherein the respiratory protective device includes a frame having a contour that maintains a breathable filter covering over a facial region of a user, wherein the frame includes at least one sensor cavity, including a first sensor cavity;

wherein the frame is configured to house a sensor network coupled to the respiratory protective device, the sensor network comprising (i) at least one sensor, including a first sensor, wherein the first sensor is disposed within the first sensor cavity to detect pressure or proximity at an interface between the frame and the facial region; and (ii) a signal processing module in operative communication with the at least one sensor, the signal processing module configured to continuously detect the pressure or proximity at the interface between the frame and the facial region via the at least one sensor for continuously monitoring fit or particulate-filtering operation of the respiratory protective device.

21. The system of claim 1, wherein the at least one sensor is made from a woven or knitted conductive fabric.

* * * * *